US011317787B2

(12) United States Patent
Hillman

(10) Patent No.: US 11,317,787 B2
(45) Date of Patent: May 3, 2022

(54) CATHETER-BASED THREE-DIMENSIONAL IMAGING USING SWEPT, CONFOCALLY ALIGNED PLANAR EXCITATION

(71) Applicant: The Trustees of Columbia University in the City of New York, New York, NY (US)

(72) Inventor: Elizabeth Marjorie Clare Hillman, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/074,751

(22) Filed: Oct. 20, 2020

(65) Prior Publication Data

US 2021/0052144 A1 Feb. 25, 2021

Related U.S. Application Data

(62) Division of application No. 16/314,752, filed as application No. PCT/US2017/041393 on Jul. 10, 2017, now Pat. No. 10,835,111.

(Continued)

(51) Int. Cl.
*H04N 5/00* (2011.01)
*A61B 1/00* (2006.01)
(Continued)

(52) U.S. Cl.
CPC ...... *A61B 1/00174* (2013.01); *A61B 1/00172* (2013.01); *A61B 1/00197* (2013.01);
(Continued)

(58) Field of Classification Search
CPC ... A61B 1/00197; A61B 1/00172; A61B 1/07; A61B 1/05; A61B 1/00174;
(Continued)

(56) References Cited

U.S. PATENT DOCUMENTS 5,074,642 A 12/1991 Hicks
5,304,810 A 4/1994 Amos
(Continued)

FOREIGN PATENT DOCUMENTS

EP 1615009 A1 1/2006
JP 2005189290 A 7/2005
(Continued)

OTHER PUBLICATIONS

Schuster et al., "Genetic dissection of structural and functional components of synaptic plasticity. I. Fasciclin II controls synaptic stabilization and growth", Neuron, Oct. 1996. vol. 17(4), p. 641-54.
(Continued)

*Primary Examiner* — Zhihan Zhou
(74) *Attorney, Agent, or Firm* — Potomac Law Group, PLLC

(57) ABSTRACT

The disclosed subject matter includes devices and systems for extending the imaging capability of swept, confocally aligned planar excitation (SCAPE) microscopes to in vivo applications. In embodiments, the SCAPE microscope can be implemented as an endoscopic or laparoscopic inspection instrument.

15 Claims, 11 Drawing Sheets

Related U.S. Application Data

(60) Provisional application No. 62/360,460, filed on Jul. 10, 2016.

(51) Int. Cl.
| | |
|---|---|
| G02B 21/00 | (2006.01) |
| G02B 3/00 | (2006.01) |
| A61B 1/05 | (2006.01) |
| A61B 1/07 | (2006.01) |
| H04N 5/225 | (2006.01) |

(52) U.S. Cl.
CPC ............... *A61B 1/05* (2013.01); *A61B 1/07* (2013.01); *G02B 3/0087* (2013.01); *G02B 21/006* (2013.01); *G02B 21/0028* (2013.01); *G02B 21/0048* (2013.01); *G02B 21/0076* (2013.01); *H04N 5/2251* (2013.01); *H04N 2005/2255* (2013.01)

(58) Field of Classification Search
CPC ......... H04N 5/2251; H04N 2005/2255; G02B 21/0028; G02B 3/0087; G02B 21/0076; G02B 21/0048; G02B 21/006
See application file for complete search history.

(56) References Cited

U.S. PATENT DOCUMENTS

| | | | |
|---|---|---|---|
| 5,442,573 A | 8/1995 | Bredberg et al. | |
| 7,068,878 B2 | 6/2006 | Crossman-Bosworth et al. | |
| 7,285,089 B2 | 10/2007 | Viellerobe et al. | |
| 8,254,020 B2 | 8/2012 | Holy et al. | |
| 8,290,358 B1 | 10/2012 | Georgiev | |
| 8,619,237 B2 | 12/2013 | Hillman et al. | |
| 9,655,523 B2 | 5/2017 | Hillman et al. | |
| 10,061,111 B2 | 8/2018 | Hillman | |
| 2001/0048082 A1 | 12/2001 | Osipchuk et al. | |
| 2003/0021016 A1 | 1/2003 | Grier | |
| 2003/0142934 A1 | 7/2003 | Pan et al. | |
| 2004/0254476 A1* | 12/2004 | Quadling | G01B 11/25 600/476 |
| 2006/0011804 A1 | 1/2006 | Engelmann et al. | |
| 2006/0182320 A1 | 8/2006 | Peszynski et al. | |
| 2007/0052958 A1 | 3/2007 | Ulrich et al. | |
| 2007/0083217 A1* | 4/2007 | Eversull | A61B 17/00234 606/114 |
| 2007/0167682 A1* | 7/2007 | Goldfarb | A61B 1/00154 600/114 |
| 2007/0272842 A1 | 11/2007 | Knebel et al. | |
| 2009/0231689 A1 | 9/2009 | Pittsyn et al. | |
| 2010/0280315 A1 | 11/2010 | Pan | |
| 2011/0121202 A1 | 5/2011 | Li et al. | |
| 2012/0113506 A1* | 5/2012 | Gmitro | G02B 21/0032 359/385 |
| 2012/0140240 A1 | 6/2012 | Hillman et al. | |
| 2012/0277288 A1 | 11/2012 | Drumm | |
| 2014/0146376 A1 | 5/2014 | Kleppe et al. | |
| 2015/0192461 A1 | 7/2015 | Chen | |
| 2015/0362719 A1* | 12/2015 | Suzuki | G02B 27/0025 359/365 |
| 2016/0213252 A1 | 7/2016 | Hillman et al. | |
| 2016/0327779 A1 | 11/2016 | Hillman | |
| 2017/0143200 A1* | 5/2017 | Majima | G02B 23/2476 |
| 2018/0001417 A1* | 1/2018 | Dulaney | H01S 3/10092 |
| 2018/0214024 A1 | 8/2018 | Hillman et al. | |

FOREIGN PATENT DOCUMENTS

| | | | |
|---|---|---|---|
| JP | 2005536312 A | 12/2005 | |
| WO | 2000016151 A1 | 3/2000 | |
| WO | 2014009080 A1 | 1/2014 | |
| WO | 2015109323 A2 | 7/2015 | |
| WO | WO-2015109323 A2 * | 7/2015 | ......... G02B 21/0064 |
| WO | 2017210159 A1 | 12/2017 | |
| WO | 2017210182 A1 | 12/2017 | |
| WO | 2018013489 A1 | 1/2018 | |
| WO | 2018052905 A1 | 3/2018 | |
| WO | 2018064149 A1 | 4/2018 | |
| WO | 2018089865 A1 | 5/2018 | |

OTHER PUBLICATIONS

Sung et al., "Three-Dimensional Holographic Refractive-Index Measurement of Continuously Flowing Cells in a Microfluidic Channel", Physical Review Applied, Feb. 2014, vol. 1(1), p. 014002.

Supplementary European Search Report for application EP 15737758 dated Sep. 28, 2017.

Swoger et al., "Light-Sheet-Based Fluorescence Microscopy for Three-Dimensional Imaging of Biological Samples", Adapted from Imaging: A Laboratory Manual (ed. Yuste). CSHL Press, Cold Spring Harbor, NY, USA, Jan. 1, 2011 copyrighted 2014 (downloaded Jun. 5, 2016).

Truong et al., "Deep and fast live imaging with two-photon scanned light-sheet microscopy", Nature Methods, 2011, vol. 8(9), p. 757-60.

Truscott et al., "Determining 3D Flow Fields via Multi-camera Light Field Imaging", Journal of Visualized Experiments: Jove, Mar. 6, 2013, vol. 73, p. 4325.

Tsai et al., "Principles, Design, and Construction of a Two-Photon Laser-Scanning Microscope for In Vitro and In Vivo Brain Imaging," Methods for In Vivo Optical Imaging, R Frostig, ed., pp. 113-171, 2002.

Van Staveren et al., "Light scattering in Intralipid-10% in the wavelength range of 400-1100 nm", Applied Optics, Nov. 1991, vol. 30(31), p. 4507-14.

Van-Der-Zee, "Measurement and modelling of the optical properties of human tissue in the near infrared, in Department of Medical Physics and Bioengineering", Thesis submitted for the degree of Ph.D. of the University of London: London, Dec. 1992.

Vaziri et al., "Ultrafast widefield optical sectioning microscopy by multifocal temporal focusing", Optics Express, Aug. 2010, vol. 18(19), p. 19645-55.

Verveer, et al., "High-resolution three-dimensional imaging of large specimens with light sheet-based microscopy", Nat Methods, Mar. 4, 2007, vol. 4(4): p. 311-3 (Abstract).

Wu et al., "Inverted selective plane illumination microscopy (iSPIM) enables coupled cell identity lineaging and neurodevelopmental imaging in Caenorhabditis elegans", Proceedings of the National Academy of Sciences, Oct. 25, 2011, vol. 108(43), pp. 17708-17713.

Xie et al., "Imaging atrial arrhythmic intracellular calcium in intact heart", Journal of Molecular and Cellular Cardiology, Nov. 2013, vol. 64, p. 120-3.

Ahrens et al., "Whole-brain functional imaging at cellular resolution using lightsheet microscopy", Nature Methods, Mar. 18, 2013, vol. 10(5): p. 413-420 (Abstract).

Akerboom et al, "Genetically encoded calcium indicators for multicolor neural activity imaging and combination with optogenetics," Frontiers in Molecular Neuroscience, vol. 6, Article 2, pp. 1-29, Mar. 2013.

Akerboom et al., "Optimization of a GCaMP calcium indicator for neural activity imaging", J Neurosci, Oct. 3, 2012, vol. 32(40), p. 13819-40.

Baik et al., "Simultaneous tracking of 3D actin and microtubule strains in individual MLO-Y4 osteocytes under oscillatory flow", Biochemical and Biophysical Research Communications, 2013, vol. 431(4), p. 718-23.

Bouchard et al., "Laser-Scanning Intersecting Plane Tomography for High Speed, Translationless 3-D Microscopy," In Journal of General Physiology, Abstracts of Papers at the Sixty-Fourth Annual Meeting of the Society of General Physiologists, Jul. 1, 2010, vol. 136(1), p. 3A, (Abstract).

Bouchard et al., "Technical considerations in longitudinal multispectral small animal molecular imaging," Journal of Biomedical Optics, vol. 12, Issue 5, p. 051601, Oct. 2007.

(56) References Cited

OTHER PUBLICATIONS

Broxton et al., "Wave optics theory and 3-D deconvolution for the light field microscope," Optics Express, Oct. 2013, vol. 21(21), p. 25418-39.
Burgess et al., "Fiber-optic and articulating arm implementations of laminar optical tomography for clinical applications," Biomedical Optics Express, Oct. 1, 2010, vol. 1(3), pp. 780-790.
Carlson et al., "In vitro functional imaging in brain slices using fast voltage-sensitive dye imaging combined with whole-cell patch recording," Nature Protocols, Jan. 2008, vol. 3(2), pp. 249-255.
Chen et al., "Ultrasensitive fluorescent proteins for imaging neuronal activity", Nature, Jul. 17, 2013, vol. 499, p. 295-300 (Abstract).
Cotton et al., "Three-dimensional mapping of microcircuit correlation structure", Frontiers in Neural Circuits, Oct. 2013, vol. 7, Article 151, pp. 1-13.
Curtis et al., "Morphology of the pupal heart, adult heart, and associated tissues in the fruit fly, *Drosophila melanogaster*". Journal of Morphology, 1999, vol. 240, pp. 225-235.
Dodt et al., "Ultramicroscopy: three-dimensional visualization of neuronal networks in the whole mouse brain", Nature Methods, Mar. 25, 2007, vol. 4(4): p. 331-336 (Abstract).
Dunsby, "Optically sectioned imaging by oblique plane microscopy", Optics Express, 16(25), Dec. 2008, 11 pgs.
Dwyer et al., "Confocal reflectance theta line scanning microscope for imaging human skin in vivo", Opt Lett, Apr. 2006, vol. 31(7), p. 942-4.
Engelbrecht et al., "Resolution enhancement in a light-sheet-based microscope (SPIM)", Optics Letters, May 2006, vol. 31(10) pp. 1477-1479.
EP Respond to Communication pursuant to Article 94(3) EPC dated Oct. 19, 2020 issued in EP App. No. 17777696.0.
Fahrbach, et al., "Rapid 3D light-sheet microscopy with a tunable lens", Optics Express, Sep. 9, 2013, vol. 21(18): p. 21010-21026 (Abstract).
Friedrich et al., "STED-SPIM: Stimulated Emission Depletion Improves Sheet Illumination Microscopy Resolution", Biophysical Journal, Apr. 2011, vol. 100(8), pp. L43-L45.
Glickfeld et al., "Cortico-cortical projections in mouse visual cortex are functionally target specific", Nature Neuroscience, Feb. 2013, vol. 16(2), p. 219-26.
Göbel et al., "Imaging cellular network dynamics in three dimensions using fast 3D laser scanning", Nature Methods, Jan. 1, 2007, vol. 4(1), p. 73-9 (Abstract).
Golan et al., "Design and characteristics of holographic neural photo-stimulation systems," Journal of Neural Engineering, vol. 6, No. 6, pp. 1-14, Oct. 2009.
Grewe, et al., "High-speed in vivo calcium imaging reveals neuronal network activity with near-millisecond precision", Nature Methods, May 2010, vol. 7(5), p. 399-405 (Abstract).
Hillman et al., "All-optical anatomical co-registration for molecular imaging of small animals using dynamic contrast", Nature Photonics, 2007, vol. 1(9): pp. 526-530.
Hillman et al., "Laminar Optical Tomography: demonstration of millimeterscale depth-resolved imaging in turbid media", Optics Letters, Jul. 15, 2004, vol. 29(14), p. 1650-1652.
Hillman, "Optical brain imaging in vivo: techniques and applications from animal to man", J Biomed Opt, 2007, vol. 12(5), p. 051402.
Holekamp et al., "Fast Three-Dimensional Fluorescence Imaging of Activity in Neural Populations by Objective-Coupled Planar Illumination Microscopy", Neuron, Mar. 13, 2008, vol. 57, pp. 661-672.

Horton et al., "In vivo three-photon microscopy of subcortical structures within an intact mouse brain", Nature Photonics, Jan. 2013, vol. 7(3), p. 205-9.
International Preliminary Report on Patentability for International Application No. PCT/US2016/042398 dated Feb. 1, 2018.
International Search Report and Written Opinion for International Application No. PCT/US2015/012076 dated May 6, 2015.
International Search Report and Written Opinion for International Application No. PCT/US2016/042398 dated Sep. 22, 2016.
International Search Report and Written Opinion for International Application No. PCT/US2017/041393 dated Oct. 9, 2017.
Jia et al., "Linear integration of spine Ca2+ signals in layer 4 cortical neurons in vivo", Proceedings of the National Academy of Sciences, Jun. 2014, vol. 111(25), p. 9277-9282.
Jing, et al., "In situ intracellular calcium oscillations in osteocytes in intact mouse long bones under dynamic mechanical loading", The FASEB Journal, Apr. 2014, vol. 28(4), p. 1582-1592.
Katona et al., "Fast two-photon in vivo imaging with three-dimensional random-access scanning in large tissue volumes". Nature Methods, Jan. 2012, vol. 9, 201-8.
Keller, et al., "Fast, high-contrast imaging of animal development with scanned light sheet-based structured-illumination microscopy", Nat Meth, 2010, vol. 7(8): p. 637-642 (Abstract).
Kepshire et al., "A microcomputed tomography guided fluorescence tomography system for small animal molecular imaging", Review of Scientific Instruments, vol. 80, Issue 4, p. 043701, Apr. 2009.
Kim, et al., "Vectorial point spread function and optical transfer function in oblique plane imaging", Optics Express, May 1, 2014, vol. 22(9), pp. 11140-11151.
Kobat et al., "Deep tissue multiphoton microscopy using longer wavelength excitation", Optics Express, Aug. 2009, vol. 17(16), p. 13354-64.
Kumar et al., "High-speed 2D and 3D fluorescence microscopy of cardiac myocytes", Optics Express, Jul. 2011, vol. 19(15), p. 13839-47.
Lavagnino et al., "Two-photon excitation selective plane illumination microscopy (2PE-SPIM) of highly scattering samples: characterization and application", Optics Express, Mar. 2013, 21(5), p. 5998-6008.
Lutz et al., "Holographic photolysis of caged neurotransmitters", Nature Methods, Sep. 2008, vol. 5(9), p. 821-7.
Mittmann et al., "Two-photon calcium imaging of evoked activity from L5 somatosensory neurons in vivo", Nature Neuroscience, 2011, vol. 14(8), p. 1089-93.
Pankajakshan et al., "Point-spread function model for fluorescense macroscopy imaging," 44th Asilomar Conference on Signals, Systems and Computers, Monterey, United States, Nov. 2010.
Planchon et al., "Rapid three-dimensional isotropic imaging of living cells using Bessel beam plane illumination", Nature Methods, May 2011, vol. 8(5), p. 417-23.
Quirin et al., "Simultaneous imaging of neural activity in three dimensions", Frontiers in Neural Circuits, vol. 8, Article 29, pp. 1-11, Apr. 2014.
Ra et al., "Three-dimensional in vivo imaging by a handheld dual-axes confocal microscope", Optics Express, May 12, 2008, vol. 16(10), pp. 7224-7232.
Radosevich et al., "Hyperspectral in vivo two-photon microscopy of intrinsic contrast", Opt Lett, Sep. 2008, vol. 33(18), p. 2164-6.
Regmi et al., "Light sheet based imaging flow cytometry on a microfluidic platform", Microscopy Research and Technique, 2013, vol. 76(11), p. 1101-7.
Schrodel et al., "Brain-wide 3D imaging of neuronal activity in Caenorhabditis elegans with sculpted light", Nat Meth, 2013, vol. 10(10), p. 1013-20.

* cited by examiner

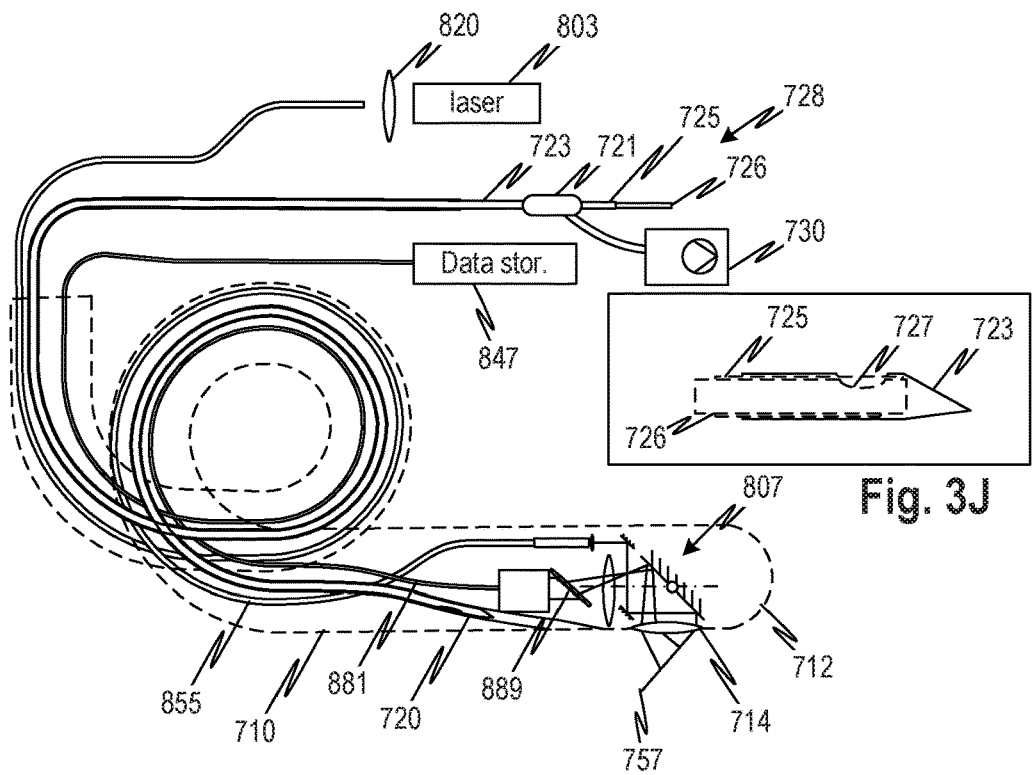
Fig. 3J
Fig. 3G
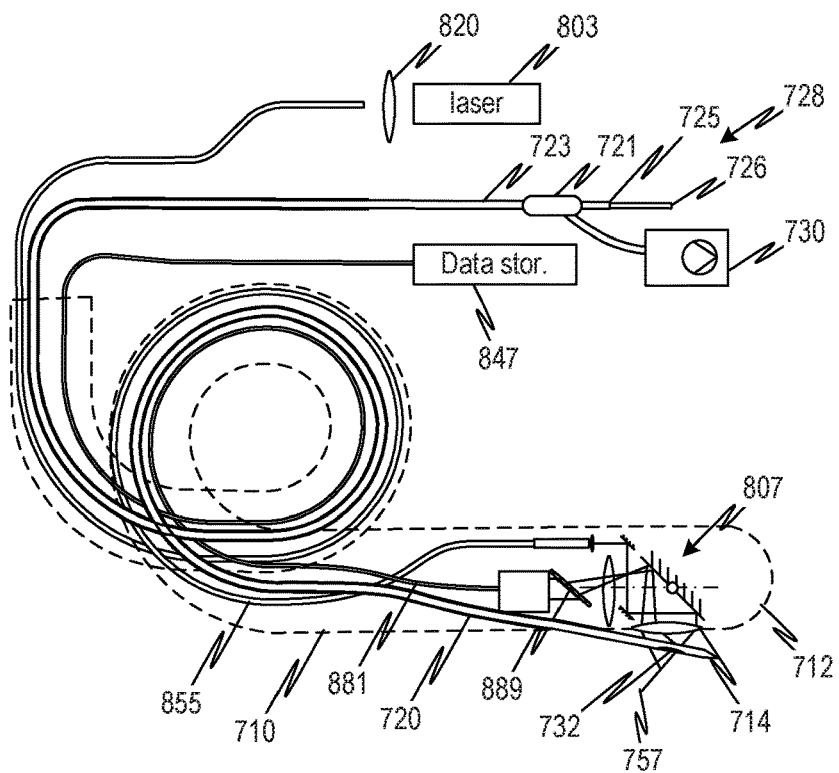
Fig. 3H

CATHETER-BASED THREE-DIMENSIONAL IMAGING USING SWEPT, CONFOCALLY ALIGNED PLANAR EXCITATION

CROSS REFERENCE TO RELATED APPLICATIONS

This application is a divisional application of U.S. application Ser. No. 16/314,752, filed Jan. 2, 2019, which is a U.S. national stage filing under 35 U.S.C. § 371 of International Application No. PCT/US2017/041393, filed Jul. 10, 2017, which claims the benefit of U.S. Provisional Application 62/360,460, filed Jul. 10, 2016, each of which is incorporated herein by reference in its entirety.

STATEMENT REGARDING FEDERALLY-SPONSORED RESEARCH

This invention was made with government support under grants NS076628, NS063228, NS053684, NS069679, NS070644, and NS061908 awarded by the National Institutes of Health, 0954796 awarded by the National Science Foundation, and W911NF-12-1-0594 awarded by Army Research Laboratory-Army Research Office. The government has certain rights in this invention.

FIELD

The present invention relates to microscopy, in embodiments, as used for endoscopic and laparoscopic examination of tissues in vivo.

BACKGROUND

Endoscopic and laparoscopic instruments may employ various imaging modalities. Some instruments provide in-vivo biological tissue imaging by accessing internal body lumens and forming images by passing illumination/excitation and image light through fiber bundles. For example, one prior art system is effectively a confocal microscope scanning a point of light across a section plane of tissue. The resolution of the prior art system, for example described in U.S. Pat. No. 7,285,089 is limited by the number of fibers. In U.S. Pat. No. 5,074,642, a fiber bundle is oscillated such that different fibers are swept across a source to scan a target tissue sample, but this system operates at a relatively slow speed. In U.S. Pat. No. 7,068,878, the distal end of the fiber is physically moved in order to scan the spot of light and simultaneously descan that spot, while the proximal end of the fiber remains stationary. WO/2000/016151 describes a device in which a source of illumination employs laser pulses in a train and sweeping fibers in a flexible fiber optic channel.

A 3-dimensional imaging system called swept, confocally-aligned planar excitation (SCAPE) microscopy has been developed as described in US20160327779, which is incorporated herein by reference in its entirety. The system forms three dimensional microscopic images at high speed by scanning excitation light and de-scanning image light onto a light detector such that multiple depths of the sample are detected at each instant. It is desirable to provide SCAPE-type advantages for imaging tissue targets in vivo, for example during surgery as a real-time optical biopsy.

One aspect of the invention is directed to a first imaging apparatus that comprises a first set of optical components having a proximal end and a distal end, wherein the first set of optical components includes an objective and a bidirectional beam relay, and wherein both angle and position information of incoming light arriving at the beam relay is preserved in outgoing light that exits the beam relay. This apparatus also comprises a second set of optical components having a proximal end and a distal end, wherein the second set of optical components includes an objective disposed at the distal end of the second set of optical components. This apparatus also comprises a scanning element that is disposed proximally with respect to the proximal end of the first set of optical components and proximally with respect to the proximal end of the second set of optical components. The scanning element is arranged to route a sheet of excitation light so that the sheet of excitation light will pass through the first set of optical components in a proximal to distal direction and project into a sample that is positioned distally beyond the distal end of the first set of optical components, wherein the sheet of excitation light is projected into the sample at an oblique angle, and wherein the sheet of excitation light is projected into the sample at a position that varies depending on an orientation of the scanning element. The first set of optical components routes detection light from the sample in a distal to proximal direction back to the scanning element. The scanning element is also arranged to route the detection light so that the detection light will pass through the second set of optical components in a proximal to distal direction and form an intermediate image plane at a position that is distally beyond the distal end of the second set of optical components. This apparatus also comprises a light detector array arranged to capture images of the intermediate image plane.

In some embodiments of the first apparatus, the beam relay is disposed at the distal end of the first set of optical components, the beam relay has a proximal end, and the objective is disposed adjacent to the proximal end of the beam relay.

In some embodiments of the first apparatus, the objective is disposed at the distal end of the first set of optical components, the beam relay has a distal end, and the distal end of the beam relay is disposed adjacent to the objective.

In some embodiments of the first apparatus, the beam relay comprises a GRIN lens.

In some embodiments of the first apparatus, the beam relay comprises a Hopkins rod lens telescope. In some embodiments of the first apparatus, the beam relay comprises a glass lens endoscope.

Some embodiments of the first apparatus further comprise a light sheet generator that expands light from a light source into the sheet of excitation light, and a beam splitter disposed between the proximal end of the second set of optical components and the scanning element. In these embodiments, the beam splitter is arranged to route the sheet of excitation light, which arrives from the light sheet generator, towards the scanning element, and the beam splitter is arranged to route the detection light, which arrives from the scanning element, into the proximal end of the second set of optical components. In some of these embodiments, the light sheet generator comprises a light source and at least one of (a) a cylindrical lens arranged to expand light from the light source into the sheet of excitation light; (b) an aspheric mirror arranged to expand light from the light source into the sheet of excitation light; (c) a spatial light modulator arranged to expand light from the light source into the sheet of excitation light; (d) a second scanning element arranged to expand light from the light source into the sheet of excitation light; and (e) an oscillating galvanometer mirror arranged to expand light from the light source into the sheet of excitation light.

Some embodiments of the first apparatus further comprise a light sheet generator that expands light from a light source into the sheet of excitation light. In these embodiments, the second set of optical components is arranged to route the sheet of excitation light, which arrives from the light sheet generator, in a distal to proximal direction towards the scanning element. In some of these embodiments, the light sheet generator comprises a light source and at least one of (a) a cylindrical lens arranged to expand light from the light source into the sheet of excitation light; (b) an aspheric mirror arranged to expand light from the light source into the sheet of excitation light; (c) a spatial light modulator arranged to expand light from the light source into the sheet of excitation light; (d) a second scanning element arranged to expand light from the light source into the sheet of excitation light; and (e) an oscillating galvanometer mirror arranged to expand light from the light source into the sheet of excitation light.

In some embodiments of the first apparatus, the intermediate image plane is stationary.

In some embodiments of the first apparatus, the second set of optical components has a first magnification in a first radial direction and a second magnification in a second radial direction that is perpendicular to the first radial direction, and the first magnification is at least 1.5 times the second magnification.

Another aspect of the invention is directed to a second apparatus that comprises a first set of optical components having a proximal end and a distal end, wherein the first set of optical components includes an objective and a bidirectional beam relay, and wherein both angle and position information of incoming light arriving at the beam relay is preserved in outgoing light that exits the beam relay. This apparatus also comprises a second set of optical components having a proximal end and a distal end, wherein the second set of optical components includes an objective disposed at the distal end of the second set of optical components. This apparatus also comprises a scanning element that is disposed proximally with respect to the proximal end of the first set of optical components and proximally with respect to the proximal end of the second set of optical components. The scanning element is arranged to route a sheet of excitation light so that the sheet of excitation light will pass through the first set of optical components in a proximal to distal direction and project into a sample that is positioned distally beyond the distal end of the first set of optical components, wherein the sheet of excitation light is projected into the sample at an oblique angle, and wherein the sheet of excitation light is projected into the sample at a position that varies depending on an orientation of the scanning element. The first set of optical components routes detection light from the sample in a distal to proximal direction back to the scanning element. The scanning element is also arranged to route the detection light so that the detection light will pass through the second set of optical components in a proximal to distal direction and form an intermediate image plane at a position that is distally beyond the distal end of the second set of optical components. This apparatus also comprises a light detector array arranged to capture images of the intermediate image plane, and a light redirector positioned to redirect at least one of the excitation light and the detection light so that a path of the excitation light and a path of the detection light are parallel.

In some embodiments of the second apparatus, the beam relay is disposed at the distal end of the first set of optical components, the beam relay has a proximal end, and the objective is disposed adjacent to the proximal end of the beam relay.

In some embodiments of the second apparatus, the objective is disposed at the distal end of the first set of optical components, the beam relay has a distal end, and the distal end of the beam relay is disposed adjacent to the objective.

In some embodiments of the second apparatus, the first set of optical elements comprises a telescope, and the beam relay is disposed proximally with respect to the telescope.

In some embodiments of the second apparatus, the first set of optical elements comprises a telescope, and the beam relay is disposed between a proximal end and a distal end of the telescope.

In some embodiments of the second apparatus, the first set of optical elements comprises a telescope, and the beam relay is disposed distally with respect to the telescope.

In some embodiments of the second apparatus, the beam relay comprises a GRIN lens. In some embodiments of the second apparatus, the beam relay comprises a Hopkins rod lens telescope. In some embodiments of the second apparatus, the beam relay comprises a glass lens endoscope.

Another aspect of the invention is directed to a third imaging apparatus. This apparatus comprises a first set of optical components having a proximal end and a distal end, wherein the first set of optical components includes an objective and a bidirectional beam relay, wherein both angle and position information of incoming light arriving at the beam relay is preserved in outgoing light that exits the beam relay. This apparatus also comprises a second set of optical components having a proximal end and a distal end, wherein the second set of optical components includes an objective disposed at the distal end of the second set of optical components. This apparatus also comprises a scanning element that is disposed proximally with respect to the proximal end of the first set of optical components and proximally with respect to the proximal end of the second set of optical components. The scanning element is arranged to route a sheet of excitation light so that the sheet of excitation light will pass through the first set of optical components in a proximal to distal direction and project into a sample that is positioned distally beyond the distal end of the first set of optical components, wherein the sheet of excitation light is projected into the sample at an oblique angle, and wherein the sheet of excitation light is projected into the sample at a position that varies depending on an orientation of the scanning element. The first set of optical components routes detection light from the sample in a distal to proximal direction back to the scanning element. The scanning element is also arranged to route the detection light so that the detection light will pass through the second set of optical components in a proximal to distal direction and form an intermediate image plane at a position that is distally beyond the distal end of the second set of optical components. This apparatus also comprises a light detector array arranged to capture images of the intermediate image plane. The beam relay comprises a plurality of beam relay segments and a plurality of articulating joints, each of the articulating joints is disposed between adjacent beam relay segments, and each of the articulating joints comprises at least one optical element configured to redirect light between the adjacent beam relay segments.

In some embodiments of the third apparatus, the beam relay is disposed at the distal end of the first set of optical components, the beam relay has a proximal end, and the objective is disposed adjacent to the proximal end of the beam relay.

In some embodiments of the third apparatus, the objective is disposed at the distal end of the first set of optical components, the beam relay has a distal end, and the distal end of the beam relay is disposed adjacent to the objective.

In some embodiments of the third apparatus, the scanning element is integrated into one of the articulating joints.

Another aspect of the invention is directed to a fourth imaging apparatus. This apparatus comprises a catheter, a first lens disposed at a distal portion of the catheter, and a scanning element that scans a sheet of excitation light towards the first lens. The first lens is arranged to route the excitation light into tissue located outside the catheter, and to route detection light arriving from the tissue back towards the scanning element, and the scanning element reflects the detection light that arrives via the first lens in a first direction. This apparatus also comprises a second lens disposed in front of the scanning element in the first direction, wherein the second lens is positioned to accept the detection light that was reflected by the scanning element, and wherein the second lens routes the detection light received from the scanning element onto a tilted intermediate image plane. This apparatus also comprises a camera optically positioned to capture images at the tilted intermediate image plane.

Some embodiments of the fourth apparatus further comprise a laser having an output, an optical fiber positioned to route light from the output of the laser through the catheter and towards the scanning element, and an optical element disposed at the distal end of the optical fiber, wherein the optical element is configured to create the sheet of excitation light from light arriving via the optical fiber. In some of these embodiments, the optical element comprises a GRIN lens. In some of these embodiments, the optical element comprises a scanning element.

Some embodiments of the fourth apparatus further comprise a light source disposed in the distal portion of the catheter, the light source having an output, and an optical element disposed in the distal portion of the catheter. The optical element creates the sheet of excitation light from light arriving from the output of the light source. In some of these embodiments, the optical element comprises a GRIN lens. In some of these embodiments, the optical element comprises a scanning element.

In some embodiments of the fourth apparatus, the camera comprises a 2D image sensor positioned at the tilted intermediate image plane.

In some embodiments of the fourth apparatus, the camera comprises a 2D image sensor positioned at a position that is remote from the tilted intermediate image plane. In these embodiments, a fiber optic bundle routes light from the tilted intermediate image plane to the 2D image sensor, and the fiber optic bundle has a distal face that is angled and positioned so as to coincide with the tilted intermediate image plane. In some of these embodiments, the fiber optic bundle comprises an n by m bundle of fibers, and m≥2n.

In some embodiments of the fourth apparatus, the camera comprises a linear image sensor positioned at the tilted intermediate image plane.

In some embodiments of the fourth apparatus, the camera comprises a linear image sensor positioned at a position that is remote from the tilted intermediate image plane. In these embodiments, a fiber optic bundle routes light from the tilted intermediate image plane to the linear image sensor, and the fiber optic bundle has a distal face that is angled and positioned so as to coincide with the tilted intermediate image plane. In some of these embodiments, the fiber optic bundle comprises an n by m bundle of fibers, and m≥2n.

In some embodiments of the fourth apparatus, the first lens has an outer face that faces distally beyond the catheter. In some embodiments of the fourth apparatus, the first lens has an outer face that is sideways-facing with respect to the catheter.

Another aspect of the invention is directed to a fifth apparatus. This apparatus comprises a first set of optical components having a proximal end and a distal end, wherein the first set of optical components includes an objective and a bidirectional beam relay, wherein both angle and position information of incoming light arriving at the beam relay is preserved in outgoing light that exits the beam relay. This apparatus also comprises a second set of optical components having a proximal end and a distal end, wherein the second set of optical components includes an objective disposed at the distal end of the second set of optical components. This apparatus also comprises a scanning element that is disposed proximally with respect to the proximal end of the first set of optical components and proximally with respect to the proximal end of the second set of optical components. The scanning element is arranged to route a sheet of excitation light so that the sheet of excitation light will pass through the first set of optical components in a proximal to distal direction and project into a sample that is positioned distally beyond the distal end of the first set of optical components, wherein the excitation light exits the first set of optical components in a sideways-facing direction with respect to a proximal-to-distal axis of the first set of optical components, wherein the sheet of excitation light is projected into the sample at an oblique angle, and wherein the sheet of excitation light is projected into the sample at a position that varies depending on an orientation of the scanning element. The first set of optical components routes detection light from the sample in a distal to proximal direction back to the scanning element. The scanning element is also arranged to route the detection light so that the detection light will pass through the second set of optical components in a proximal to distal direction and form an intermediate image plane at a position that is distally beyond the distal end of the second set of optical components. This apparatus also comprises a light detector array arranged to capture images of the intermediate image plane, and a tool that is movable between a retracted position and an extended position. When the tool is moved to the extended position, a tip of the tool is positioned within a field of view of the imaging apparatus.

In some embodiments of the fifth apparatus, the beam relay is disposed at the distal end of the first set of optical components, the beam relay has a proximal end, and the objective is disposed adjacent to the proximal end of the beam relay.

In some embodiments of the fifth apparatus, the objective is disposed at the distal end of the first set of optical components, the beam relay has a distal end, and the distal end of the beam relay is disposed adjacent to the objective.

In some embodiments of the fifth apparatus, the tool comprises a tissue sampling needle. In some embodiments of the fifth apparatus, the tool comprises a dye injection tool.

Another aspect of the invention is directed to a sixth apparatus. This apparatus comprises a catheter, and a first lens disposed at a distal portion of the catheter. The first lens has an outer face that is sideways-facing with respect to the catheter. This apparatus also comprises a scanning element that scans a sheet of excitation light towards the first lens, wherein the first lens is arranged to route the excitation light into tissue located outside the catheter, and to route detection light arriving from the tissue back towards the scanning element, and wherein the scanning element reflects the detection light that arrives via the first lens in a first direction. This apparatus also comprises a second lens disposed in front of the scanning element in the first direction, wherein the second lens is positioned to accept the detection light that was reflected by the scanning element, and wherein the second lens routes the detection light received from the scanning element onto a tilted intermediate image plane. This apparatus also comprises a camera optically positioned to capture images at the tilted intermediate image plane, and a tool that is movable between a retracted position and an extended position. When the tool is moved to the extended position, a tip of the tool is positioned in front of the outer face of the first lens.

In some embodiments of the sixth apparatus, the tool comprises a tissue sampling needle. In some embodiments of the sixth apparatus, the tool comprises a dye injection tool.

Another aspect of the invention is directed to a first method of imaging a sample. This method comprises projecting a sheet of excitation light into a sample through a beam relay, wherein the sheet of excitation light is projected into the sample at an oblique angle, and wherein the sheet of excitation light is projected into the sample through the beam relay at a position that varies with time. This method also comprises routing detection light arriving from the sample into a proximal end of an optical system that includes the beam relay. This method also comprises forming a stationary intermediate image plane at a distal end of the optical system, and capturing images of the intermediate image plane at a plurality of times.

In some embodiments of the first method, the sheet of excitation light is projected into the sample at a position that varies with time depending on an orientation of a scanning element, the routing step is implemented by the scanning element, and each of the images of the intermediate image plane corresponds to a different orientation of the scanning element.

In some embodiments of the first method, the beam relay includes a plurality of articulating joints.

Some embodiments of the first method further comprise redirecting at least one of the excitation light and the detection light so that a path of the excitation light and a path of the detection light are parallel.

Methods, devices, and systems are described for adapting SCAPE for use in imaging tissue targets in vivo, for example during surgery as a real-time biopsy.

Objects and advantages of embodiments of the disclosed subject matter will become apparent from the following description when considered in conjunction with the accompanying drawings, wherein like reference numerals represent like elements.

BRIEF DESCRIPTION OF THE DRAWINGS

FIGS. 3G, 3H, and 3J show an endoscope configuration that includes the imaging system of FIG. 3C and also provides a sampling catheter that is positioned and oriented to sample tissue at the point of inspection of the sideways-directed microscope.

DESCRIPTION OF EMBODIMENTS

A variety of embodiments for implementing imaging using swept, confocally aligned planar excitation (SCAPE)

are disclosed in publications WO 2015/109323 and US 2016/0327779, each of which is incorporated herein by reference in its entirety. In most of the embodiments described in those two applications the objective is positioned on the tissue being imaged so that the oblique image plane can be scanned through the tissue. But in certain anatomic situations, it may not be possible to bring the objective into contact with the tissue being imaged. For example, it may not be possible to image a human kidney using the embodiments disclosed in the two applications identified above because the kidney is not close enough to the surface of the subject.

The present application describes a number of approaches for capturing images at anatomic locations that are located at some distance below the surface of a living subject such as within a body lumen. Access to locations below the outer surface of a subject may be obtained via an extension such as a beam relay or a distally-located miniaturized detector. The former may allow image capture, scanning and de-scanning to occur on the proximal side of the beam relay. In use, the device is inserted through a natural opening or a surgically created opening below the outer surface of the subject's body. In some embodiments, the extension arm may be rigid, and in other embodiments the extension arm may be flexible.

In some embodiments, an image relay is added to one of the designs disclosed in the two applications identified above beneath the objective. Note that as used herein, laparoscope refers to devices that relay light and angular properties of light using optics and are embodied in the examples by straight supports or articulating supports. As used herein, endoscope refers to flexible devices that transmit image information through flexible light conduits. Existing laparoscopes that are designed for use in front of cameras can be used to relay images from the distal to the proximal ends. These devices may be used in conjunction with a SCAPE system. One way to implement a laparoscope is by using a straight laparoscope either using spaced lenses or a Hopkins-type series of rod relay lenses.

Figure 1A:
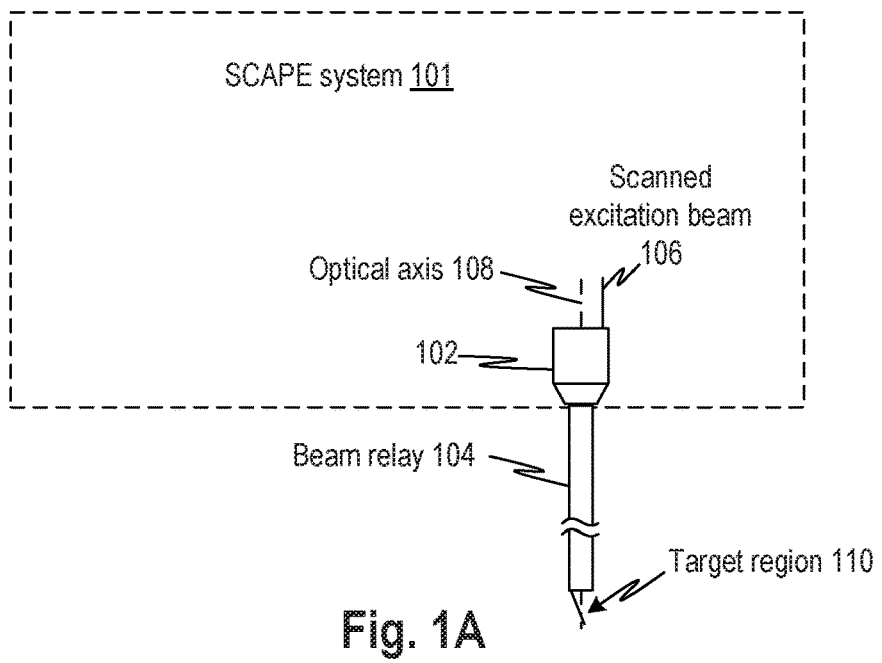
FIG. 1A shows a generalized SCAPE imaging system extended by a beam relay thereby forming an endoscopic microscopic inspection instrument, according to embodiments of the disclosed subject matter.

FIG. 1A shows a generalized SCAPE imaging system 101 extended by a beam relay 104 thereby forming a laparoscopic microscopic inspection instrument 100, according to embodiments of the disclosed subject matter. The SCAPE system 101 includes a forward objective 102 that relays an excitation pencil beam or sheet beam through an oblique range of positions, each illuminating multiple depths and providing selectivity of the illumination region by virtue of the narrow beam or sheet of light. Light from multiple depths illuminated by the sheet or beam is captured by the same forward objective 102 and de-scanned by the SCAPE system 101 as described in the patent publications incorporated by reference above. The beam relay 104 effectively maps the imaged and illuminated region of the forward objective 102 down the length of the beam relay 104 to a target region 110 at its end according to principles that will be readily understood by those of skill in the art in conjunction with the further details described below.

Figure 1B:
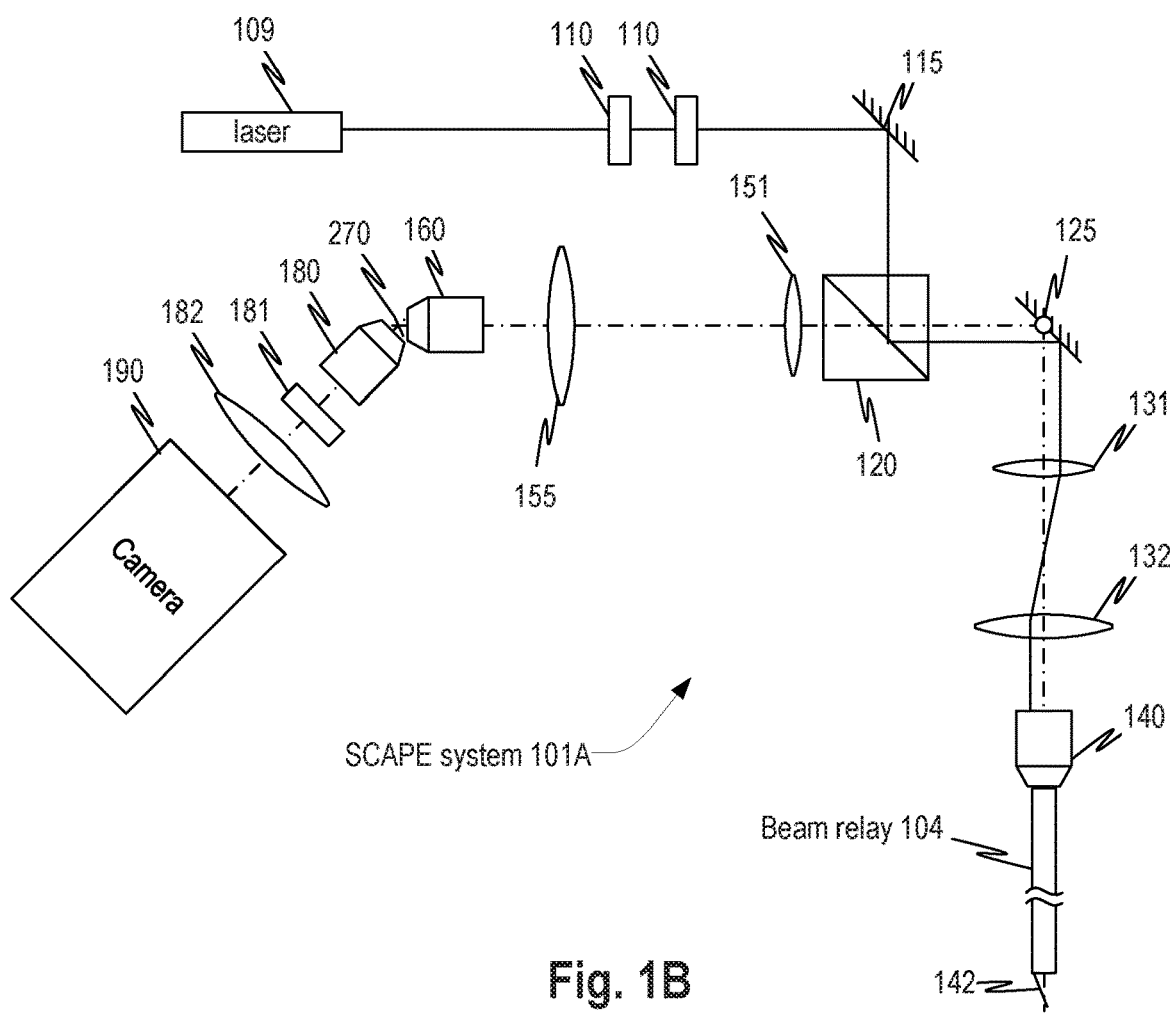
FIG. 1B shows a particular X-swept two-dimensional light sheet-type SCAPE imaging device that may be used in place of the generalized SCAPE imaging system of FIG. 1A to form an endoscopic microscopic inspection instrument, according to embodiments of the disclosed subject matter.

FIG. 1B shows a particular X-swept two-dimensional light sheet-type SCAPE imaging device that may be used in place of the generalized SCAPE imaging system of FIG. 1A to form a laparoscopic microscopic inspection instrument, according to embodiments of the disclosed subject matter.

FIG. 1B is a first embodiment of a SCAPE system 101A that may be combined with a beam relay 104. Light from the light source (e.g., laser 109 or a LED) is routed towards a beamsplitter 120 by one or more routing mirrors 115, and expanded from a pencil beam into a sheet by one or more cylindrical lenses 110. The sheet of light (more accurately, a precursor of a sheet as the sheet is ultimately formed by the forward objective as will be understood by those of skill in the art) is reflected by the beam splitter 120 towards a scanning element 125. In some embodiments, this scanning element 125 comprises a rapidly moving galvanometer mirror. In alternative embodiments, the scanning element 125 could be implemented using a rapidly moving prism or any of a variety of alternative designs including MEMS light guides, SLM, etc. that will be apparent to persons skilled in the relevant arts or apparent from the references incorporated above.

After being rerouted by the scanning element 125, the sheet of light continues down the excitation arm in a proximal to distal direction through a first set of optical components (e.g., lenses 131, 132 and objective 140). The sheet of light then enters the beam relay 104 and is ultimately conveyed to a sample region at an oblique angle to penetrate a tissue sample along the Z axis, resulting in a sheet of light 142. When the scanning element 125 moves (e.g., due to motion of the galvanometer mirror), it causes the position of the sheet of light 142 within the sample to translate. Thus, the position of the sheet of excitation light within the sample varies depending on the orientation of the scanning element 125.

The excitation light may excite fluorescence in a sample or it may simply illuminate the sample, and the illuminated region is imaged. The path of the image light from the sample to the detector first passes through the first set of optical components 131-140 in a distal to proximal direction and back to the scanning element 125. From there, the image light passes through the dichroic beam splitter 120 and into the detection arm. The detection arm includes a second set of optical components (e.g., lenses 151, 155 and imaging elements 160). The image light passes through these components 151-160 in a proximal to distal direction and forms an intermediate image plane 270. Because the sheet of light entered the sample at an oblique angle, the intermediate image plane corresponding to the section of the sample illuminated by the light sheet 142 will be tilted with respect to the optical axis of lenses 151, 155. One of the advantages of this configuration of SCAPE is that the position of the intermediate image plane 270 remains stationary, regardless of changes in the position of the sheet of light 142 within the sample.

In alternative embodiments, instead of using the cylindrical lenses 110 to convert the pencil-shaped beam from the light source (e.g., laser 100) into a fan-shaped sheet, a Powell lens or an SLM may be used to perform that function. In alternative embodiments, one of the routing mirrors 115 may be replaced by a second scanning mirror oriented to scan the pencil shaped beam so as to create a virtual sheet of light. Note that as used herein, the term "sheet of light" includes these virtual sheets of light as well as true sheets of light (e.g., light sheets formed using one or more cylindrical lenses and/or a Powell lens, etc.). An example is described below.

In order to capture the image that appears at the tilted intermediate image plane 270, a variety of approaches may be used. In the FIG. 1B embodiment, a magnifier is used to rotate and expand the image and route it to a light detector array (e.g., camera 190). This magnifier includes a third objective 180 and additional optical components (e.g., lens 182 and optional long pass filter 181). The light detector array (e.g., camera 190) captures images of the tilted intermediate image plane 270.

In some embodiments, the first set of optical components 131-140 in the excitation arm matches the second set of optical components 151-160 in the detection arm. The same scanning element 125 is used in both the excitation path and the detection path. This configuration is advantageous because it cancels out certain optical distortions that are difficult to cancel using alternative approaches. For example, if the magnification of the second set of optical components 151-160 in the detection arm is higher than the magnification of the first set of optical components 131-140 in the excitation arm, the image that appears at the tilted intermediate image plane 270 will be distorted. In some situations, this distortion may be acceptable or even desirable (e.g., when the differences in magnification are used to reduce the angle of the tilted intermediate image plane).

In embodiments where the optical components in the excitation arm match the optical components in the detection arm, the scale of the tilted intermediate image plane 270 will match the scale of the sheet of light 142 that extends into the sample (after accounting for refractive index differences of immersion media). For example, 1 micron in the Z direction at the sample (i.e., the depth direction, which is the direction at which the excitation light propagates within the sample) will correspond to 1 micron at the tilted intermediate image plane 270. And 1 micron in the Y direction at the sample (i.e., the width direction, which is the direction that is perpendicular to the page in FIG. 1B) will correspond to 1 micron at the tilted intermediate image plane 270 in the direction that is perpendicular to the page of FIG. 1B.

When capturing light, cameras that have larger pixels are often used because larger pixels capture more light than smaller pixels. For example, many conventional cameras have pixels that measure 7 μm×7 μm. If it is desired to achieve resolution of 1.4 μm at the sample, and a camera that has 7 μm pixels is used, it is necessary to magnify the image by a factor of 5 to expand the 1.4 μm pixels at the tilted intermediate image plane 270 to match the 7 μm pixels in the camera 190. This can be accomplished by the magnifier that includes the third objective 180 and the additional optical components 181, 182. (Note that resolution at the sample in the X direction can be selected by the system designer and is controlled by scanning because when the scanning element 125 moves, the sheet of light 142 will move within the sample by a corresponding amount.) By placing the magnifier 180-182 in front of the camera 190, we obtain 1.4 μm resolution at the sample, and each of those 1.4 μm pixels maps onto a corresponding 7 μm pixel at the camera 190.

The FIG. 1B embodiment has a number of advantages. It relies on a single galvanometer scanner 125 and a dichroic beam splitter 120. (In alternative embodiments, a rotating or oscillating polygon may be used in place of these components.) The orthogonal alignment of the excitation arm and the detection arm makes this embodiment easier to assemble and align. Distortion is avoided because the optical components in the excitation arm match the optical components in the detection arm, as explained above.

The FIG. 1B embodiment however, has a significant disadvantage. Because the intermediate image plane 270 is tilted with respect to the optical axis of lenses 151, 155, the camera 190 and magnifier 180-182 in front of the camera 190 are mounted to match the angle of the tilt of the intermediate image plane 270. As a result, a large portion of the light traveling to the left after it passes through the second objective 160 in the detection arm will not be captured by the camera 190. This lost light corresponds to lost numerical aperture, signal, and a corresponding decrease in signal-to-noise ratio and resolution.

One possible approach for overcoming the above-identified problem (i.e., that a large portion of light is lost in the FIG. 1 embodiment) would be to position the 2D camera sensor at the position of the tilted intermediate image plane 270. In that configuration, the light traveling to the left out of the second objective 160 would fall directly on the 2D camera sensor, in which case most of that light would be captured. But this configuration has a different problem. Because conventional high-sensitivity camera sensors have large pixels (e.g., 7 μm), and because the image at the tilted intermediate image plane is the same size as the sheet of light 142 in the sample, this would mean that the best resolution that can be obtained at the sample would be 7 μm resolution in both the Y direction and the Z direction. And 7 μm resolution may not be sufficient to resolve the structures of interest in the sample. Increasing the magnification in the detection arm introduces distortion, and also increases the steepness of the tilt angle of the intermediate image plane 270, which causes a variety of other problems.

An approach for overcoming the above identified problems is to place a camera sensor with smaller pixels (e.g., on a 1.4 μm pitch) at the tilted intermediate image plane 270. While this approach can provide usable images, the sensitivity of the device is drastically reduced. This is because the area of 7 μm×7 μm camera pixels is 25 times larger than the area of camera pixels that measure 1.4 μm×1.4 μm. And this 25× reduction in area reduces the sensitivity of the device.

Figure 1C:
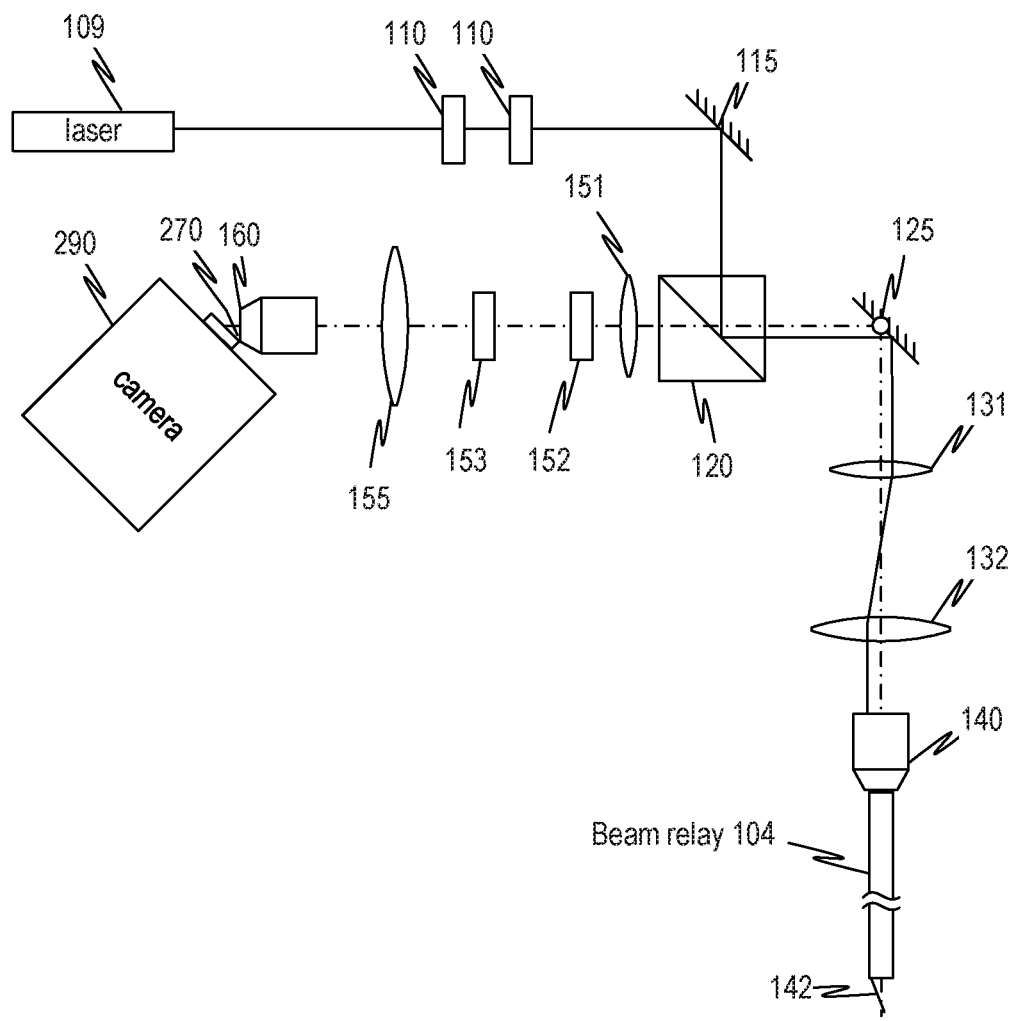
FIG. 1C shows an X-Y swept light beam-type SCAPE imaging device that may be used in place of the generalized SCAPE imaging system of FIG. 1A to form an endoscopic microscopic inspection instrument, according to embodiments of the disclosed subject matter.

FIG. 1C shows a swept light beam-type SCAPE imaging device that may be used in place of the generalized SCAPE imaging system of FIG. 1A and combined with a beam relay 104 to form a laparoscopic microscopic inspection instrument, according to embodiments of the disclosed subject matter.

The FIG. 1C embodiment uses asymmetric magnification in the detection path to provide a solution to the problems identified above. More specifically, in the FIG. 1C embodiment, the second set of optical components has a first magnification in a first radial direction and a second magnification in a second radial direction that is perpendicular to the first radial direction, and the first magnification is at least 1.5 times the second magnification. This may be accomplished (as it is in the FIG. 1C embodiment) by incorporating cylindrical optical components 152, 153 within the second set of optical components 151-160 in the detection arm. (Note that the FIG. 1C embodiment is similar to the FIG. 1B embodiment, except that cylindrical optical components are added to the detection arm in FIG. 1C.)

In the FIG. 1C embodiment, the asymmetric magnification is implemented using cylindrical lenses 152, 153 to increase the magnification of the image at the tilted intermediate image plane 270 in the Y direction only (i.e., the width direction that is perpendicular to the page). In these embodiments, the magnification in the first radial direction in the second set of optical components corresponds to magnification of the width dimension of the detection light. Notably, increasing magnification in the Y direction does not introduce the distortions discussed above. The camera 290 can then be positioned so that its image sensor is located at the tilted intermediate image plane 270, which avoids the losses associated with the off-axis third objective 180 in the FIG. 1B embodiment.

In some embodiments, the second set of optical components has both isotropic components (e.g., spherical lenses 151, 155) that magnify the image at the tilted intermediate plane in all radial directions and cylindrical components 152, 153 that magnify the image at the tilted intermediate plane in the radial direction that corresponds to the Y direction only. The isotropic magnification of the first set of optical components 131-140 preferably matches the isotropic magnification of the second set of optical components 151-160, but the optical characteristics in the direction that is perpendicular to the page will not match due to the cylindrical lenses 152, 153 that appear in the second set of optical components only.

In these embodiments, any magnification that occurs in the first set of optical components 131-140 is preferably symmetric and uniform in all radial directions. This uniform magnification is preferably the same as the magnification in the X direction that occurs in the second set of optical components 151-160.

When asymmetric (e.g., unilateral) magnification is used, rectangular pixels of the light sheet 142 in the sample map onto square pixels in the camera 290. For example, in a system where the camera has 7 μm pixels, and the cylindrical lenses 152, 153 provide 5× magnification in the Y direction, rectangular regions that measure 1.4 μm×7 μm at the light sheet 142 in the sample will map onto camera pixels that measure 7 μm×7 μm. In this example, we obtain 1.4 μm resolution in the Y direction at the sheet of light 142 in the sample; and we obtain 7 μm resolution in the Z direction at the sheet of light 142. (The resolution in the X direction can be set to any desired value by adjusting scanning because scanning shifts the position of the light sheet 142 within the sample.) Even though the resolution is only 7 μm resolution in the depth Z direction at the sample, this technique provides far better multiplane imaging than competing techniques. In addition, this approach maintains sensitivity because cameras with large pixels are used. This configuration advantageously captures almost all of the detected light, corresponding to a higher NA detection. It provides better resolution, higher throughput, and improved signal-to-noise. In addition, alignment requires only positioning of the camera, and there is no need it to align any of the additional optical components (e.g., components 180-182 that appear in the FIG. 1 embodiment but are not included in the FIG. 1C embodiment).

In another example, in a system where the camera has 7 μm pixels and the cylindrical optical components provide 2.5× magnification in the Y direction, rectangular regions that measure 2.8 μm×7 μm at the light sheet 142 in the sample will map onto camera pixels that measure 7 μm×7 μm. Other magnification values for the Y direction (e.g., between 2× and 8×) may be used in alternative embodiments.

Because the resolution is different in the Z direction than the Y direction in these embodiments, we can take advantage of this difference to increase the read-out rate from the camera sensor. For example, in the FIG. 1B embodiment, if a 1000-micron range is desired along Y at the sample and 300-micron depth range Z, and a total of 500 pixels is desired along the Y direction (i.e., 2 μm resolution), it will be necessary to use 150 pixels along Z because the pixels are square. This corresponds to 150 rows at the camera. Because the readout speed in many commercially available cameras depends on the number of rows and not the number of columns, that 150 pixels in the Z direction dictates the camera's read-out rate.

In contrast, in the FIG. 1C embodiment, the magnification of each dimension is scaled independently and the number of pixels in the Z direction is decreased due to the lower resolution in that direction. As a result, each frame has fewer rows in the Z direction. For example, when 2× magnification is used, only 75 rows need to be acquired in the Z direction. This means that the FIG. 1C embodiment can capture frames at twice the speed of the FIG. 1B configuration, but still cover the same 300-micron depth without sacrificing resolution in the Y direction (or the X direction, which is governed by scanning).

In some embodiments, the ability to implement asymmetric magnification can be used to trade off lateral and depth resolution—e.g., to have good pixel resolution along y and x while reducing the number of rows used in z. This asymmetric magnification could permit faster speed acquisition at higher x-y resolutions with lower resolution in z (or vice versa). This additional degree of freedom would also allow adjustment of magnification within the telescopes 131, 132 and 151, 155 without changing the angle of the intermediate image plane, and thus the camera angle.

In some embodiments, a similar approach may be used to trade off resolution in a given direction. For example, the system may be switched to a lower resolution in order to achieve a higher frame rate. Conversely, the system may be switched to a lower frame rate in order to achieve a higher resolution.

Optionally, these embodiments may be configured to take advantage of the fact that the camera read out is fastest at the center of the camera chip for particular cameras (e.g., the Andor Zyla camera). In these embodiments, it is preferable to re-position the image on the camera for samples where the range of depths to be imaged is different. For example, to obtain 300 rows in a thick sample, the sample can be maintained at the narrowest part of the light sheet, in which case the image can be positioned from the middle −150 to the middle +150 position on the camera chip. In another example, where a 50-row acquisition is being implemented, the image should be positioned in the middle −25 to middle +25 portion of the camera chip. In this latter situation, the image is translated up 125 rows on the camera). This translation may be implemented, for example, using steering mirrors on the detection arm, which can optionally be incorporated into an image splitter.

Note that in the FIG. 1C embodiment, asymmetric magnification is implemented using cylindrical lenses 152, 153 to increase the magnification of the image at the tilted intermediate image plane 270 in the Y direction only (i.e., the direction that is perpendicular to the page). But in alternative embodiments, the asymmetric magnification may be implemented in different directions. For example, asymmetric magnification may be used to increase the magnification of the image in the Z direction, but leave the image non-magnified in other directions. Optionally, the orientation of the image sensor/camera in these embodiments may be rotated 90 degrees so that the direction having decreased resolution aligns with the rows of the image sensor. This means that fewer rows can be read out for each frame, which can be relied on to increase the frame rate of the system as discussed above.

In some alternative embodiments, instead of using cylindrical lenses 152, 153 to provide the asymmetric magnification, alternative optical components (e.g., an SLM and/or aspheric mirrors) may be used to increase the magnification of the image at the tilted intermediate image plane 270 in the desired direction.

In a variation of the FIG. 1C approach, cylindrical optical components are included in the detection arm in order to implement asymmetric magnification, and a sensor that has small pixels (e.g., 1.4 μm by 1.4 μm) is placed at the tilted intermediate image plane 270. The magnification provided by the cylindrical optical components will magnify a square region that measures 1.4 μm on each side onto a plurality of pixels at the sensor. For example, when 5× magnification is used, a square 1.4 µm region on the light sheet 142 in the sample will be projected onto five adjacent pixels on the camera 290 (which together occupy a region that measures 1.4 µm×7 µm). The data in these five adjacent pixels can then be binned together. This technique may be used to trade off resolution between the Z and Y directions and/or trading off sensitivity with resolution. Note that when this technique is used, the total number of pixels in the camera 290 is increased. If the pixel count exceeds the pixel count of commercially available sensors, multiple sensors may be mounted at the tilted intermediate image plane 270 in a tiled configuration.

Figure 1D:
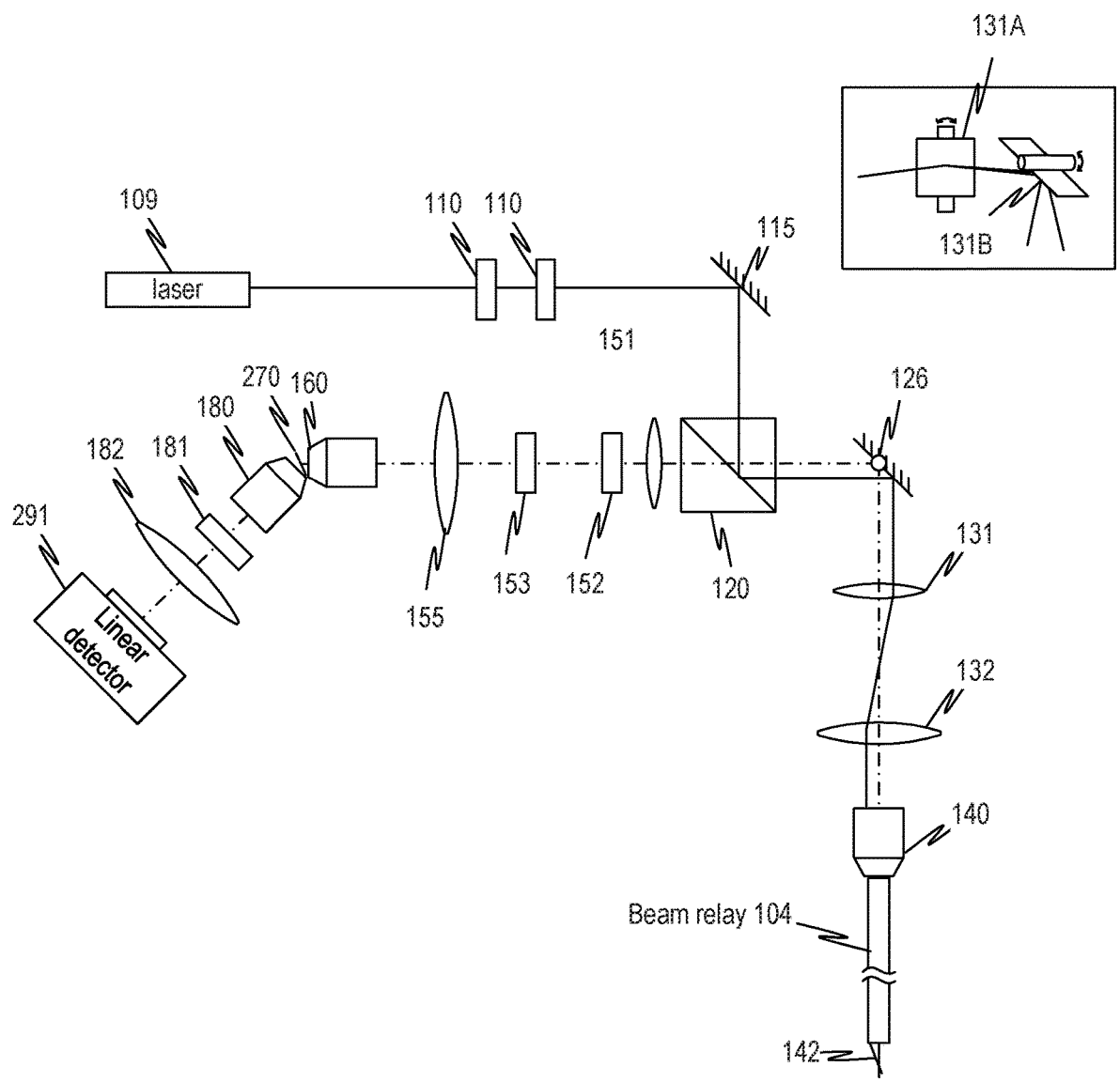
FIG. 1D shows an X-Y swept light beam-type SCAPE imaging device that may be used in place of the generalized SCAPE imaging system of FIG. 1A to form an endoscopic microscopic inspection instrument, according to embodiments of the disclosed subject matter.

FIG. 1D is similar to the embodiment of FIG. 1C, except that a linear detector 291 is used instead of the 2D detector 290. Notably, this embodiment does not rely on a virtual sheet of light that is scanned all at once. Instead, this embodiment relies on a single line having a depth in the Z direction that is scanned in two dimensions in order to trace through a three-dimensional volume. This single line is ultimately imaged onto a tilted intermediate image plane 271 that is similar to the tilted intermediate image plane 270 of the FIG. 1C embodiment, except that the tilted intermediate image plane 271 is a one-dimensional line instead of a two-dimensional plane. This one-dimensional line is ultimately imaged onto the linear detector 291. The same third objective 180 and additional components 181, 182 that were used in the FIG. 1B embodiment are used in this embodiment, and those components work the same way as the corresponding components in the FIG. 1B embodiment. The scanning device 126 may be a single element that scans in two axes, or it may include multiple elements as illustrated at 131A and 131B to achieve a similar effect.

Figure 1E:
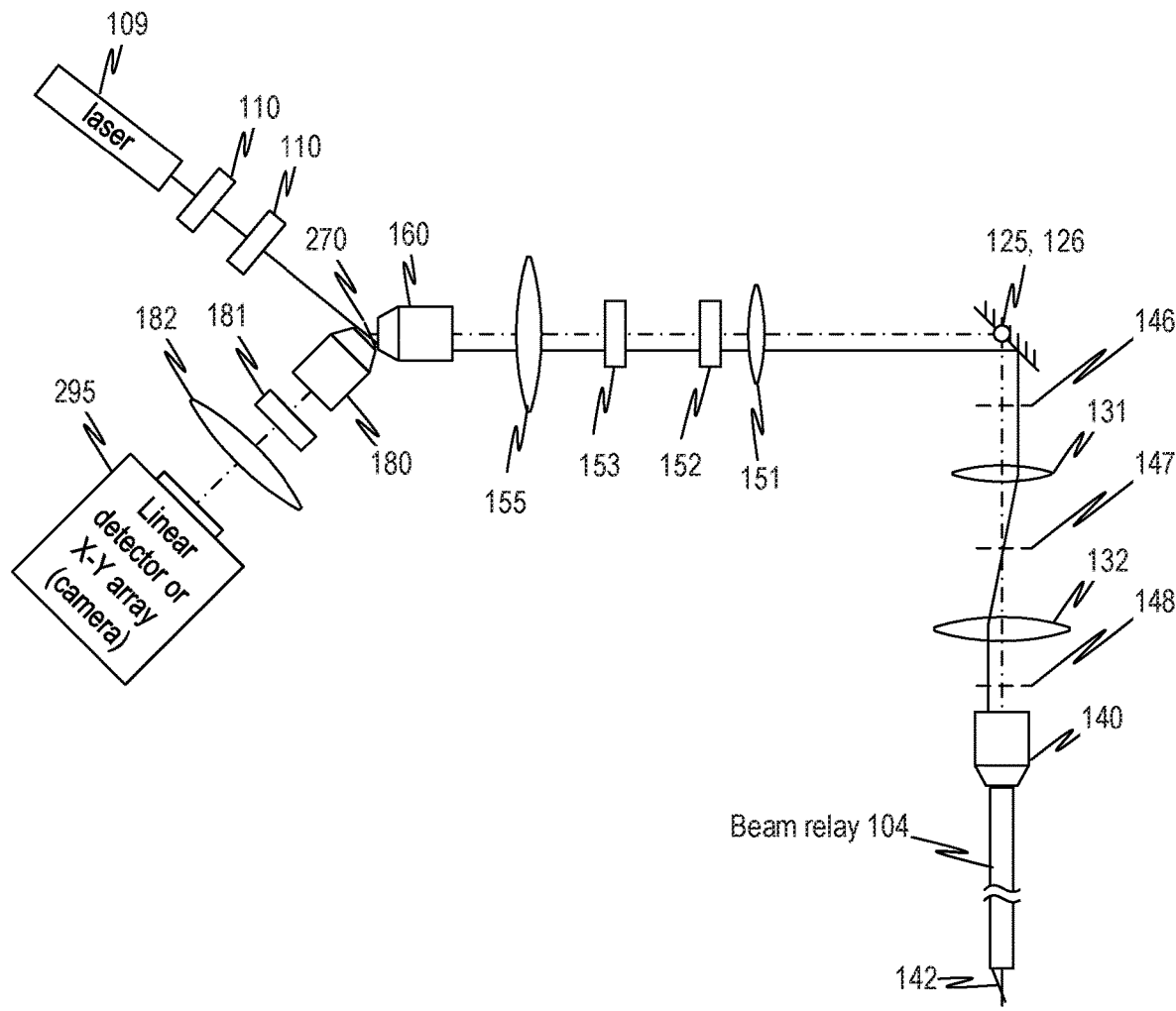
FIG. 1E shows an X-Y swept light beam-type SCAPE imaging device that may be used in place of the generalized SCAPE imaging system of FIG. 1A to form an endoscopic microscopic inspection instrument, according to embodiments of the disclosed subject matter highlighting an alternative illumination beam configuration.

FIG. 1E depicts an alternative approach for introducing the sheet of light into the system, which may be used as a replacement for the light-sheet introduction approach depicted in any of FIGS. 1B-1D described above. In this alternative approach, light from the laser 109 may be shaped into a sheet (e.g., by cylindrical lenses 110, or by a Powell lens or SLM) and directed into the imaging optical components 151-160 at an angle and at the edge of the element 160 (which may be chosen to match the properties of the primary objective 140) as will be understood from the disclosures incorporated by reference above and by those with a general knowledge of oblique plane microscopy. This may avoid the need for a beam splitter (See 120 in previous embodiments) to merge the excitation/illumination light. Separation of light such as fluorescent light of different colors or reflectance light in the return beam may be accomplished using a filter 181 such as a long pass filter to discriminate reflectance light from fluorescent light in the returned light from the target.

Figure 1F:
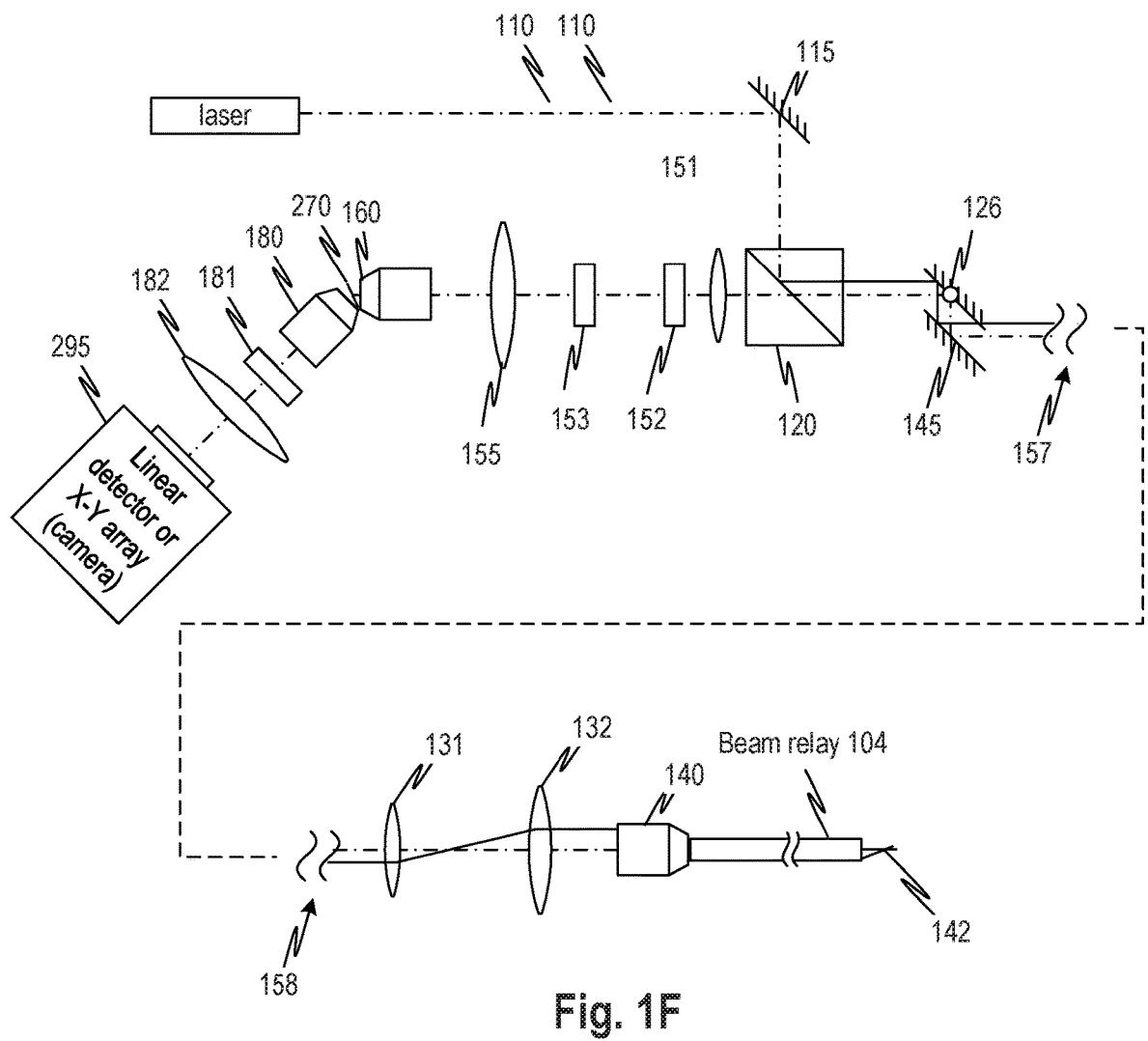
FIG. 1F shows an X-Y swept light beam-type SCAPE imaging device that may be used in place of the generalized SCAPE imaging system of FIG. 1A to form an endoscopic microscopic inspection instrument, according to embodiments of the disclosed subject matter.

FIG. 1F shows a straightened beam path based on the embodiment of FIG. 1C or FIG. 1D where an auxiliary reflector 145 is placed in the beam path after the scanning mirror 125 or 126 to allow the excitation and detection light to continue along a straight path. This may facilitate incorporation of optical elements of SCAPE into a laparoscope, thereby reducing the number of optical elements required. The same feature may be used with the embodiment of FIG. 1C. Note that instead of a scanning reflector, acousto-optic modulator, a prism or dual reflector may be used for scanning and de-scanning (as indicated in the references incorporated above) thereby permitting the beam path to be straightened without the use of an additional reflector.

Figure 2A:
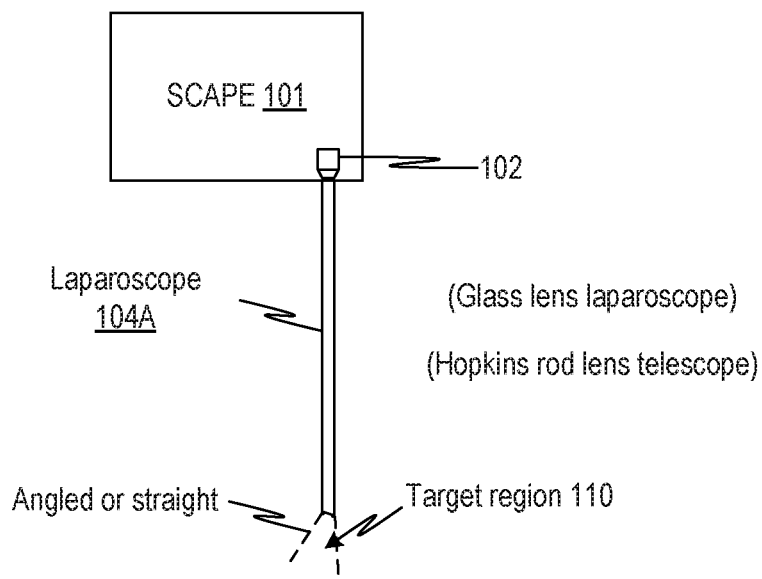
FIG. 2A shows an embodiment of a beam relay that may be used with any of the foregoing embodiments, the beam relay being based on an endoscope with two examples identified, a glass lens and a Hopkins rod lens type endoscope.

FIG. 2A shows an embodiment of a lens-based beam relay that may be used with any of the foregoing embodiments. Examples of suitable lens-based beam relays include beam relays built from glass lenses or a Hopkins rod lens type laparoscope 104A. The optics at the end of the laparoscope 104A may be directed slightly away from the axis or straight along the axis.

Figure 2B:
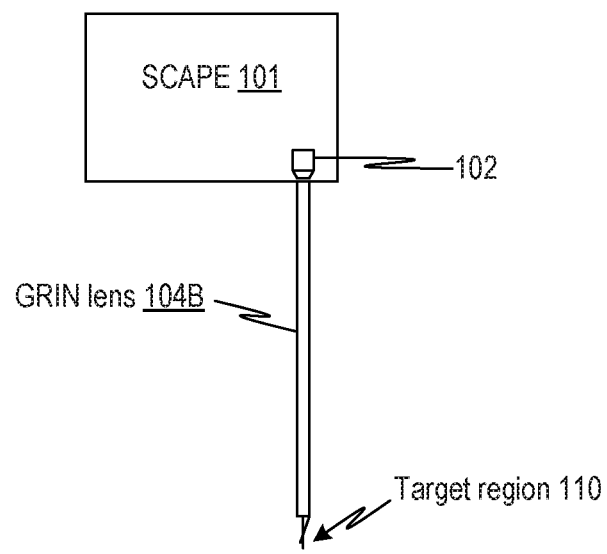
FIG. 2B shows another embodiment of a beam relay that may be used with any of the embodiments of FIGS. 1A-1C, the beam relay being based on a GRIN lens.

FIG. 2B shows another embodiment of a beam relay that may be used with any of the embodiments of FIGS. 1A-1F, the beam relay being built from one or more GRIN lenses 104B. In some embodiments, the GRIN lens 104B may replace the forward objective of the SCAPE system 101 or it may be used in combination with an objective lens or other optical elements to provide the described result of a swept beam or sheet of light and oblique imaging. In alternative embodiments (not shown), the beam relay could be positioned between the telescope 131, 132 and the primary objective 140 (shown in FIGS. 1B-1F), or the beam relay may be included within the telescope itself.

Figure 2C:
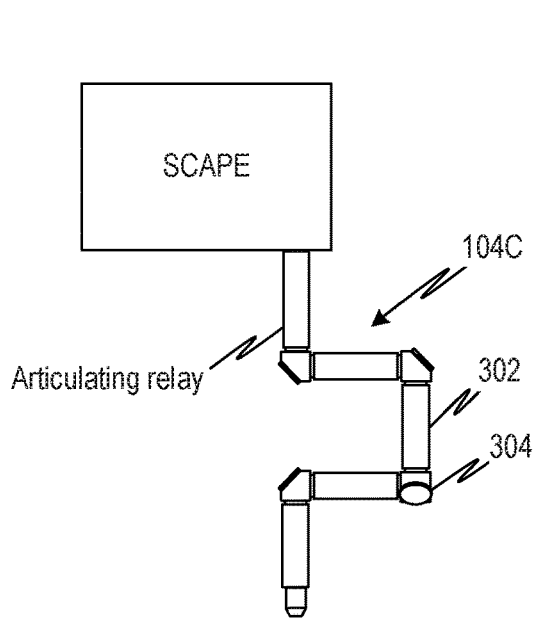
FIG. 2C shows another embodiment of a beam relay that may be used with any of the embodiments of FIGS. 1A-1C, the beam relay employing an articulated arm having multiple mirrors that pivot around the optical axis to relate the beam along a path of the arm.
Figure 2D:
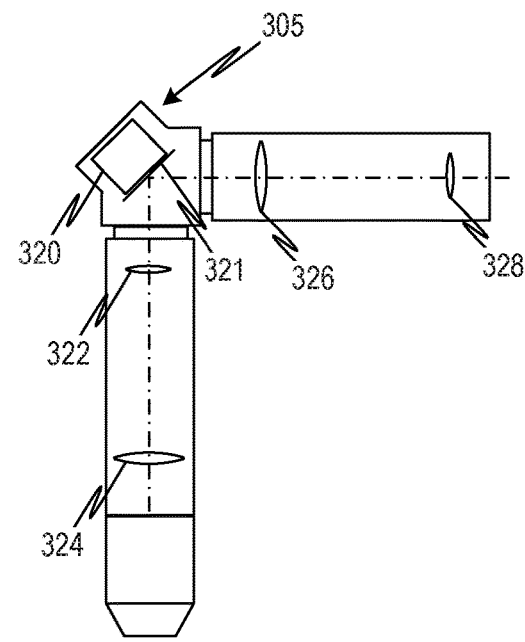
FIG. 2D illustrates that links can contain beam conditioning optics as in the embodiments of FIGS. 1B through 1F.
Figure 2E:
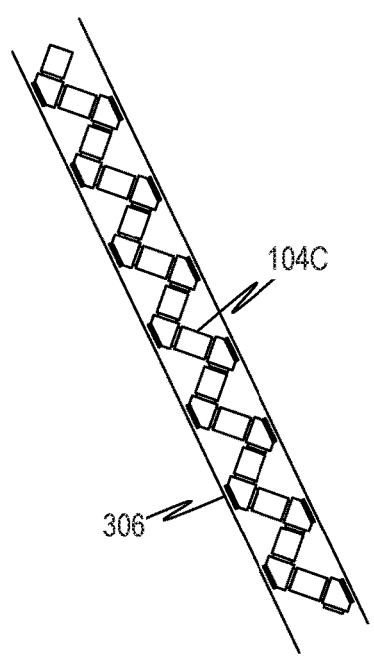
FIG. 2E illustrates how in articulating arm can be enclosed within a flexible sheath to form a flexible endoscope or laparoscope.

FIG. 2C shows another embodiment of a beam relay that may be used with any of the embodiments of FIGS. 1A-1F, the beam relay employing an articulated arm having multiple mirrors that pivot around the optical axis to relay the excitation and image light along a path of the arm. The arm may consist of multiple fixed length links with reflectors (e.g., prisms, mirrors) at the joints where each link 302 pivots relative to adjacent links 302. The links 302 may be short or long. FIG. 2D illustrates that links can contain beam conditioning optics may be used as in the embodiments of FIGS. 1B through 1F. As shown in FIG. 2E, the arm may be encased in a flexible sheath 306. The latter may contain a steering mechanism in order to form a steerable laparoscope embodiment.

Figure 3A:
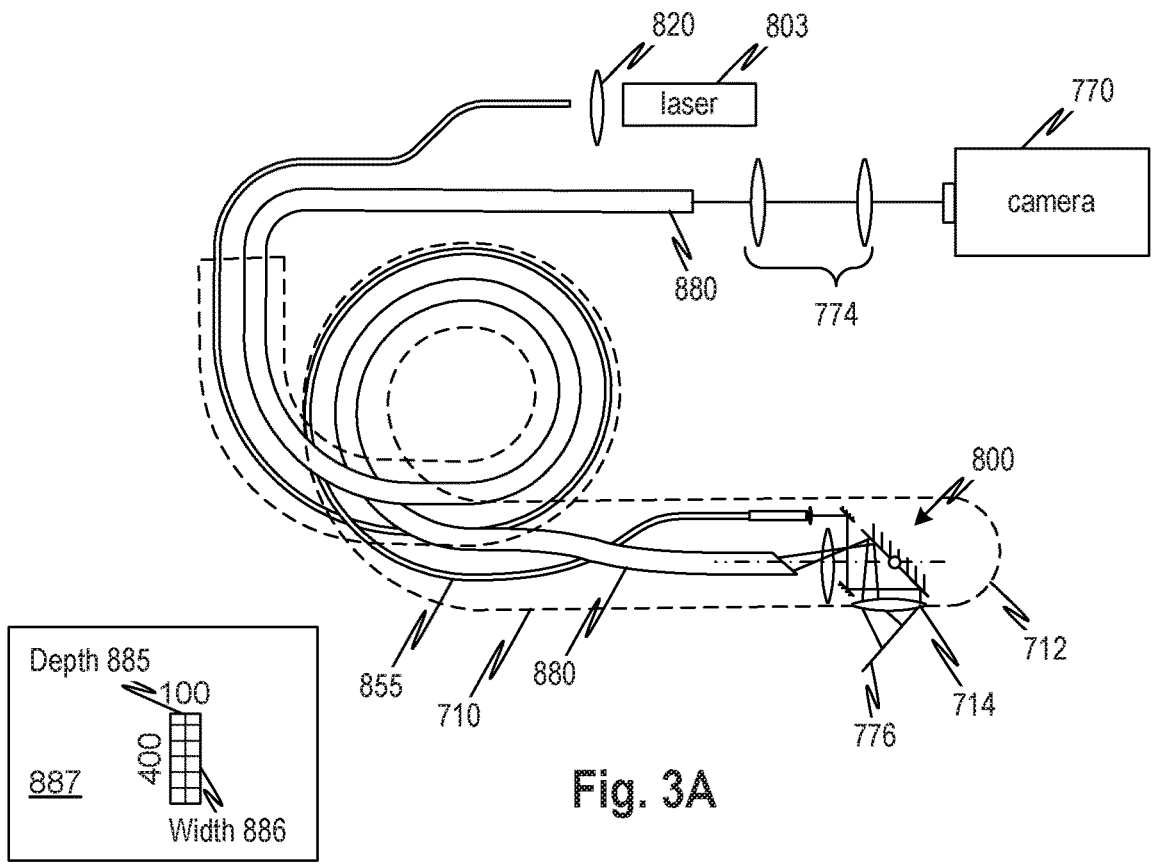
FIG. 3A shows a SCAPE system where the scanning and de-scanning elements are miniaturized and incorporated in the tip of an endoscope, with excitation light being carried by light guides such as flexible fiber bundles and where a light sheet is swept in a single dimension, according to embodiments of the disclosed subject matter.

FIG. 3A shows a SCAPE system where the scanning and de-scanning elements as well as others are miniaturized and incorporated in the tip of an endoscope as an imaging head 800. It may be designed to fit within the confines of a sheath 710 that measures between 2 and 10 mm in diameter in some embodiments, or between 2 and 5 mm in diameter. Excitation light is carried by a light guide 855 and image light is returned through a fiber bundle 880 and imaged on a camera 770 by imaging optics 774. A light sheet 776 may be swept in a single dimension as discussed in the detailed view of imaging head 800 with reference to FIG. 3D. The light guides 855 and 880 may be carried in a sheath 710 that either has a rounded tip 712 is depicted in FIG. 3A, or a tip with a different shape (not shown). A final lens 714 of the forward objective may seal the sheath 710 to form a smooth surface that can be brought into abutment with target tissue after insertion. A steering mechanism (not shown) may be provided within at least a portion of the sheath 710.

Optionally, the entire imaging head 800 may be configured to move in a repeatable and steady manner so as to implement a roving scan mode. Images captured using this roving scan mode may subsequently be stitched together either within the imaging head itself or externally. Roving scans may be implemented in various embodiments using, for example, pullback of the tip, mechanical steering, and/or rotation of the optical components about a longitudinal axis of the catheter.

At 887, it is illustrated that the number of fibers required for imaging may be reduced (as compared to a symmetric fiber bundle based confocal microendoscope device) by asymmetric transmission in the fiber of a smaller number of depths 885 which correspond to one dimension of the SCAPE "snapshot," as should be clear from the disclosure and the references incorporated above. That is, each position of the scanned excitation sheet provides return light (reflection, fluorescent, or a combination) for multiple depths. The multiple depths may be developed across the narrow (e.g., 100 fiber) dimensions of the fiber array with the other dimension (width) 886 consuming a larger number of fiber layers (e.g., 400). This allows the fiber bundle to be smaller and less complex. The larger dimension does not consume any fibers because that dimension is developed in time on the image projected on the stationary fiber bundle as should be clear from published descriptions of SCAPE as well as the present disclosure.

Figure 3B:
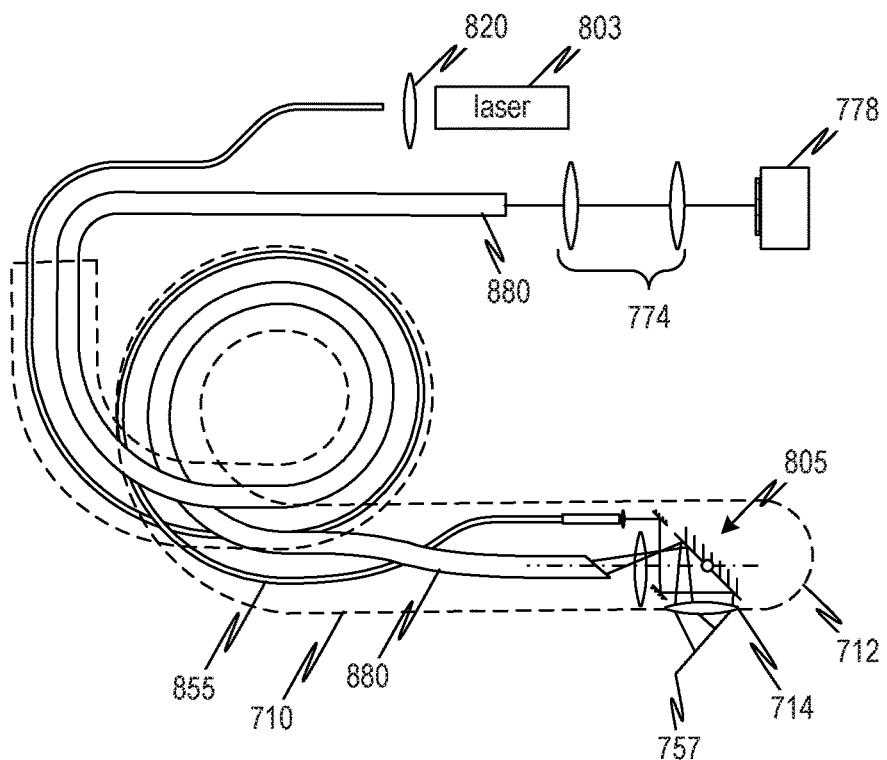
FIG. 3B shows a SCAPE system where the scanning and de-scanning elements are miniaturized and incorporated in the tip of an endoscope, with excitation light being carried by light guides such as flexible fiber bundles, and where a light beam is swept in two dimensions, according to embodiments of the disclosed subject matter.

FIG. 3B shows a SCAPE system that is similar to that of FIG. 3A, but where a linear light detector array 778 is used instead of a camera and the imaging head 805 employs a scanning element that scans in two dimensions instead of only one such that a pencil beam 757 is scanned laterally in two dimensions. In the SCAPE system of FIG. 3B, the imaging head 805 has a two-dimensional scanning/de-scanning element (or elements).

Figure 3C:
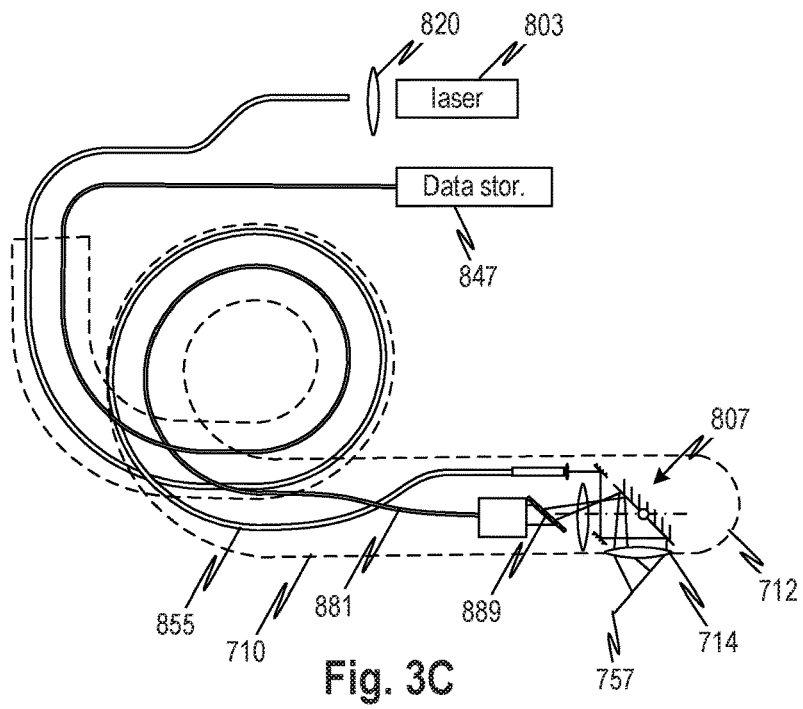
FIG. 3C shows a SCAPE system where the scanning and de-scanning elements are miniaturized and incorporated in the tip of an endoscope along with a light detector, with excitation light being carried by a light guide and sample pixel data being read out through a conductive cable, according to embodiments of the disclosed subject matter.

FIG. 3C shows a SCAPE system that is similar to that of FIG. 3A except that a light detector array 889 is positioned in the imaging head 807 rather than at the proximal end. A cable 881 transmits data to a data store 847. In other respects, the device may be as in the embodiment of FIG. 3A. In alternative embodiments, a pencil beam may be formed and a linear detector may be used as in the embodiment of FIG. 3B. In that case, the linear detector would be located in the imaging head. The reduced size of the linear detector may provide advantages for miniaturization.

Figure 3D:
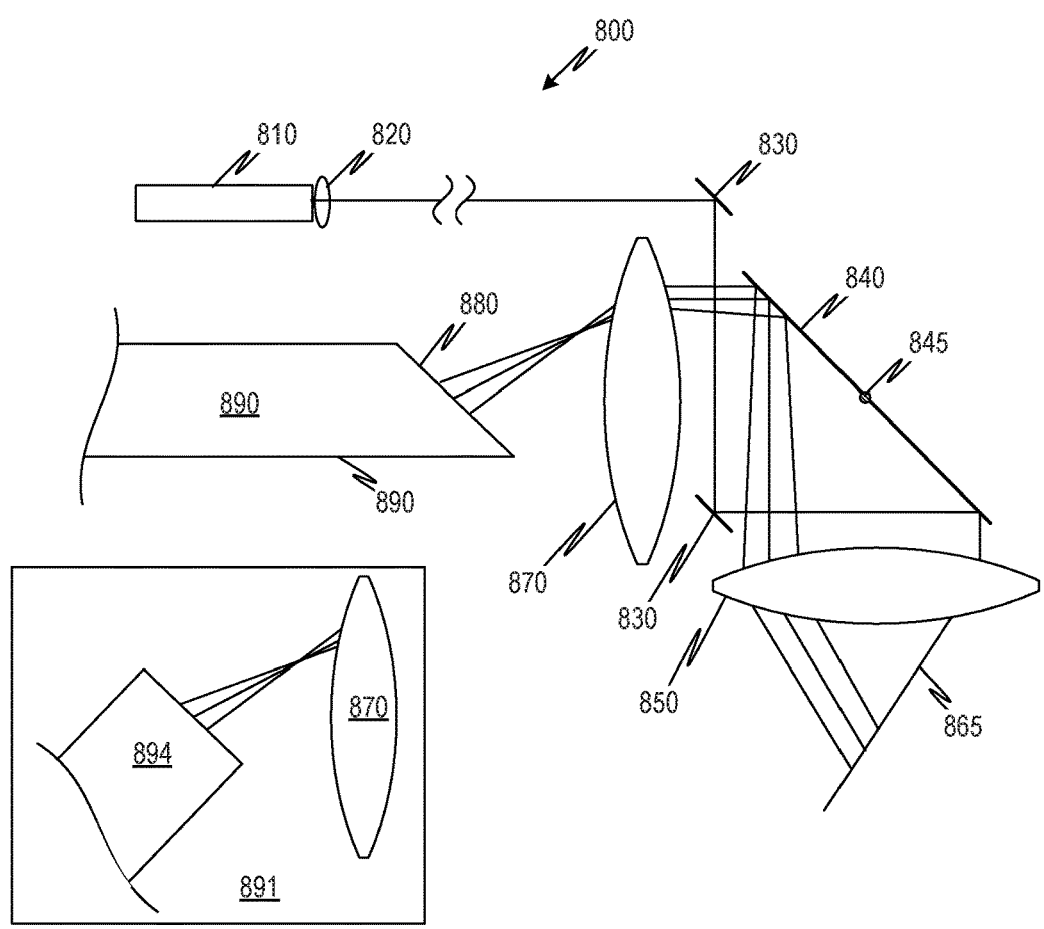
FIGS. 3D through 3F show details of imaging heads for use with the embodiments of FIGS. 3A through 3C, according to further embodiments of the disclosed subject matter.

FIG. 3D shows the imaging head 800 of the FIG. 3A embodiment in more detail. The size may be, for example between 2 and 10 mm in diameter in embodiments. In the illustrated embodiment, excitation light arrives via a fiber 810 and a mini lens 820 conditions the output of the fiber 810 to form a sheet of light at 865. Note that GRIN lenses may be used for this purpose. Optionally, a linear bundle may be used to tune the sheet width and/or the numerical aperture via the illumination at the proximal end of the fiber bundle. The light that exits the mini lens 820 will ultimately form the sheet of light 865. This precursor to this sheet of light 865 is directed by mirrors 830 onto a scanning mirror 840. At 891, it is shown that the fiber bundle 894 can have a polished end that is perpendicular to the fiber bundle (in contrast to the embodiment of 890). Here the fiber bundle 894 may be curved so that it can follow the endoscope.

The scanning mirror 840 may be implemented using a MEMS scanner that partially rotates around the illustrated center point 845 to make a scan pattern. The scan pattern causes the illumination beam to pass through objective lens 850 and into the tissue to form the sheet of light 865 within the tissue. The position of the sheet of light 865 within the tissue will depend on the angle of the scanner 840. The tissue may emit fluorescent light and/or reflect light in response to the sheet of light 865, and the fluorescent light may be collected by lens 850 and routed back to the scanner 840. From there it is directed through lens 870 to form a tilted image plane 880 incident on the front face of the fiber bundle 890, from where it is conveyed to an imaging device 770. Preferably, the front face of the fiber bundle 890 is tilted at an angle that matches the tilt of the intermediate image plane. This provides automatic de-rotation of the image.

In some embodiments, a camera sensor may be positioned so as to coincide with the tilted image plane 880, so that light from the tilted image plane 880 falls directly on the pixels of the camera sensor. In these embodiments, the camera sensor is preferably a two-dimensional camera sensor with small pixels (e.g., on the order of 1 μm). Signals from the camera sensor 880 are electrically transmitted out of the catheter 805 for processing by an image processor (as shown in FIG. 3C).

In alternative embodiments, the image at the tilted image plane 880 may be transmitted out of the catheter 805 via a fiber-optic bundle 890 with a beveled input edge that is angled to match the tilt of the tilted image plane 880. This fiber-optic bundle 890 relays the image from the tilted image plane 880 to a camera located at the proximal end of the catheter 805. In some embodiments, the fibers in the bundle 890 are tapered to terminate at a camera with large pixels (e.g., 7 μm×7 μm) located at the proximal end of the catheter. Coarse images could be obtained using a bundle of fibers that contains a 50×250 bundle. Higher-resolution images can be obtained if more fibers are used (e.g., 100×500 fibers or more). Optionally, these embodiments may be combined with a roving motion of the field of view so that a relatively small number of lateral pixels (e.g., 250) may be stitched together into a desired larger field of view without sacrificing resolution.

The imaging apparatus of FIG. 3D may be implemented using a catheter and a first lens 850 disposed at a distal end of the catheter. A scanning mirror 840 scans a sheet of light towards the inner surface of the first lens 850. The first lens 840 routes light arriving from the scanning mirror 840 into tissue located outside the catheter 805, and routes fluorescent (or reflected) light from the tissue back towards the scanning mirror 840. The scanning mirror 840 reflects the returning light that arrives via the first lens 850 in a first direction. A second lens 870 is disposed in front of the scanning mirror 840 in the first direction, and the second lens 870 is positioned to accept the returning light that was reflected by the scanning mirror 840. The second lens 870 routes the returning light received from the scanning mirror 840 onto a tilted intermediate image plane 880. A camera is optically positioned to capture images at the tilted intermediate image plane 880. In these embodiments, the sheet of light may optionally be generated by a laser and a GRIN lens 820 and/or a laser and a fiber optic bundle 810.

In these embodiments, the camera may optionally comprise a 2D image sensor positioned at the tilted intermediate image plane 880. Alternatively, the camera may optionally comprise a 2D image sensor positioned at a position that is remote from the tilted intermediate image plane 880, plus a fiber optic bundle 890 that routes light from the tilted intermediate image plane 880 to the remote 2D image sensor.

Figure 3E:
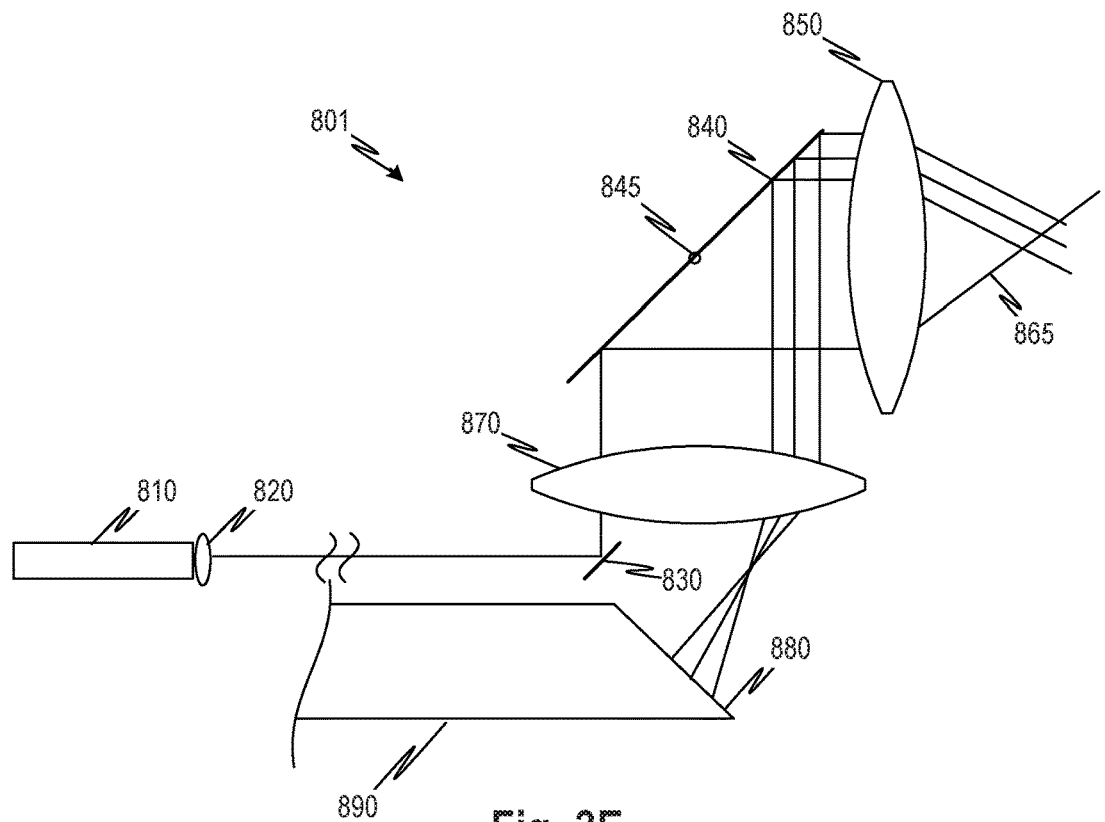
Figure 3F:
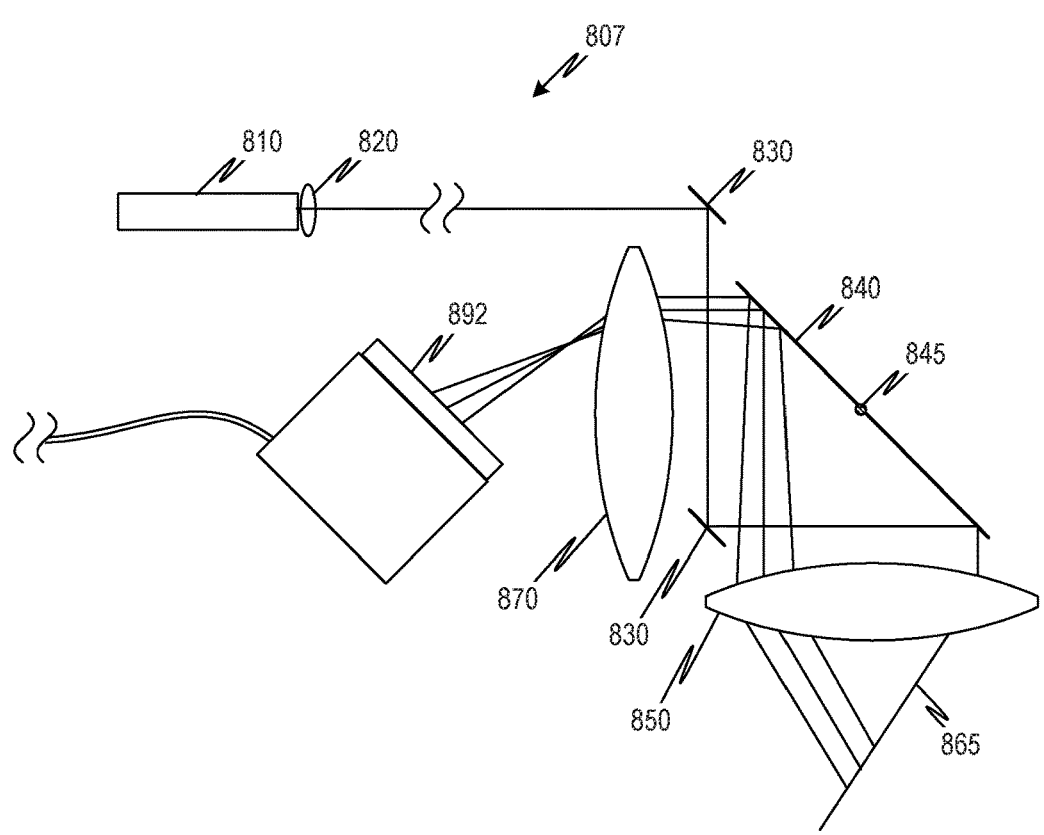

FIG. 3E shows a variation of an imaging head 801 which is similar to imaging head 800 except that lenses 850 and 870 as well as the scanning mirror 840 is rotated to image tissue at the forward tip of the endoscopic device (i.e., the endoscopic device looks forward of the tip rather than to the side). The imaging head 801 may be used with any of the foregoing embodiments. FIG. 3F shows details of an imaging head 807 in which the light detector (a linear array or two-dimensional array) 892 is positioned within the imaging head 807 region to avoid the need for a fiber bundle 890. A wide variety of alternative approaches for redirecting the aim of the endoscopic device towards different directions may also be used.

FIGS. 3G-3J show an endoscope with a sampling tool 728, which may be of any type but by way of example, a vacuum biopsy catheter 728 is shown. See closeup of tip at FIG. 3J. An outer catheter 723 holds a vacuum drawn by a vacuum pump 730 which connects and seals through a seal junction 721. An inner sheath is operable to draw a cutting edge over a sample drawn in to a recess at 732. A wire has a sample chamber 727 at its end and may be removed and replaced for the acquisition of multiple samples. As indicated, the sampling tool 728 may be positioned and oriented so that when extended as shown in FIG. 3H, it can sample the region of tissue that is acquired by the imaging device as indicated by the position of the distal-most lens 714. The sampling tool may be replaced by a dye injection device, laser marking device or other tool to form other embodiments. The distally-located detector array 889 embodiment of FIG. 3C may be advantageously combined with other tools because it may provide more room and less stiffness to the combined endoscopic device than an optical fiber. Note that although the sampling tool 728 is described in connection with FIGS. 3G-3J, similar sampling tools may be added to many of the other embodiments described above.

In any of the embodiments described above in connection with FIGS. 3A-3C, instead of routing light from an external laser through the catheter using an optical fiber 855, that configuration may be replaced by a light source (e.g., a laser diode or LED, not shown) that is disposed distally within the confines of the sheath 710 and powered by wires that run through the catheter.

For clarification and further elaboration, FIGS. 1A and 2A, in combination, show SCAPE systems implemented using a laparoscope-like rigid imaging conduit, for example using a sequence of relay lens components. Such a laparoscopic relay will preserve both angle and position of light. The laparoscope can relay the SCAPE geometry (or Fourier equivalent) at relatively high NA through the laparoscope to a distal end thereof. The SCAPE components (including the scanners) may be positioned on the proximal end of the laparoscope such that the laparoscope is configured to transmit the output/input of the object at the end of the laparoscope, effectively functioning as a relay device.

The laparoscope relays light from the SCAPE system down to the distal end of the laparoscope and vice versa. The laparoscope preserves both the angle and position information of the light, effectively shifting the light patterns at the distal end of the laparoscope up to the proximal end of the laparoscope.

In alternative embodiments (not shown), the objective may be moved down beyond the distal tip of the inspection device (i.e., distally beyond the beam relay), in which case the light pattern that is transmitted through the device would be the pattern from the proximal end of the objective. When the objective is used at the distal end of the device, miniaturization of the objective is desirable. In these devices, a laparoscope may be effectively formed. Examples of suitable objectives for use at the distal end of the laparoscope in these embodiments include GRIN lenses and mini lenses. In these embodiments, the beam relay can also serve as the primary telescope, such that the conduit is relaying light directly from the scanner. Further, a small scanning element could be housed within the same conduit such that the detection telescope could also form a part of the relaying conduit.

For clarification and further elaboration, FIGS. 1A and 2B, in combination, show SCAPE systems implemented using a laparoscope-type lens-based relay. A SCAPE system implemented using a rigid GRIN lens may be useful when shorter distances are required. GRIN lenses also preserve both angle and position of light. The GRIN lens relays the SCAPE geometry to the distal tip of the extension arm and, as indicated, may also serve as all or part of the objective lens. The objective in this embodiment may be moved down beyond the distal tip of the laparoscope, in which case the image that is transmitted through the laparoscope would be the image from the proximal end of the objective. Examples of suitable objectives for use at the distal end of the GRIN lens in these embodiments also include GRIN lenses and mini lenses. Optionally, when the objective is moved down to the distal tip, the optics at the distal end may be configured to steer the beams and/or change focus dynamically.

For clarification and further elaboration, FIGS. 1A and 2C, 2D, in combination, show SCAPE systems implemented using an articulated arm configuration. This embodiment may be useful for lasers that cannot be transmitted through glass fibers. The articulating arm configuration is used for $CO_2$ lasers for example. The articulated arm relays the SCAPE geometry to the distal tip of the extension arm. An example of a suitable construction for the articulated arm appears in Fiber-optic and articulating arm implementations of laminar optical tomography for clinical applications, Sean A. Burgess et al., Biomedical Optics Express, Vol. 1, Issue 3, pp. 780-790 (2010), which is incorporated herein by reference.

Imaging fiber bundles relay the position of light from one end to the other, but will not preserve propagation angle. However, they can be very small and flexible. Such fiber bundles are used in the CellVizio endomicroscopy system to permit single plane confocal microscopy. While scanning on the proximal end of a fiber bundle is not promising because the angle information is destroyed, fiber bundles could be used to relay the final image to a proximal camera if scanners and optics can be positioned at the tip. A benefit of using fiber bundles is that, assuming adequate acceptance angle and small enough fibers, image rotation can be achieved by using a bevel at the distal tip and a flat face at the proximal side. Lenses at the distal end could also feasibly do image rotation if necessary (full or partial), possibly tunable to assist with focusing. Note, that the same fiber bundle could be used to relay illumination light, and even shape it appropriately.

Because scanning on the proximal end is not promising, distal scanning may be used in conjunction with fiber bundles. Distal scanning has been demonstrated using MEMs type scanners by several groups (Chris Contag (Stanford), Jonathon Liu (U Washington) and Tom Wang (Michigan)) including 'theta scanning' (line-scan) confocal microscopy.

For clarification, the embodiment of FIG. 3A uses a fiber bundle with distal scanning. Many designs could be used to achieve this scanning—so long as basic requirements for focal planes are maintained. It is only necessary to scan the scanning element (mirror in this embodiment) at the desired volume-per-second rate (e.g., 10 Hz, which is easily manageable for a MEMS scanner). One example of a suitable distal scanner appears in Three-dimensional in vivo imaging by a handheld dual-axes confocal microscope by Hyejun Ra et al., Optics Express Vol. 16, Issue 10, pp. 7224-7232 (2008), which is incorporated herein by reference in its entirety. As shown in FIG. 3E, in alternative configurations, a head-on view may be implemented, which may be more desirable due to the short working distance in certain anatomic locations.

Scanning at the distal end may be implemented in two directions (x-y scanning) or in one direction only (x scanning), One of the benefits of using x-y scanning distally, rather than just a unidirectional x scan is that it reduces the number of fibers needed in the bundle. When x-y scanning is implemented distally, only a linear fiber bundle would be needed, with the number of fibers equal to the number of depths in the image volume. X-Y resolution would then be achieved by x-y scanning. Although this increases the needed speed of the distal scanners (usual frame rate would equal the volume rate), the fewer fibers will make the conduit much smaller and cheaper. The detector would then only need to be a linear detector (e.g., a line scan camera or an APD or SPAD array), or could even be separate independent detectors (e.g., PMTs or APDs) where each records the x-y image at a given depth plane (with each fiber from the bundle breaking out to each detector). In embodiments, 20 detectors (depths) may be provided, and no camera is required. Image rotation may be achieved simply by beveling/angling the linear bundle at the distal end.

Using cameras or detector arrays with sufficient speed, sensitivity, small size and safety, permit an imaging conduit or fiber bundle to be avoided with the camera/detector positioned at the tip (along with scanning) while signal is relayed electronically/digitally to an external device for storage, display, etc. The embodiment of FIG. 3C shows an example. Optionally, wireless communication may be used for this relay function. Thus, the cable 881 may be eliminated. A wide variety of alternative designs could be used to achieve this distal scanning, so long as basic requirements for focal planes are maintained. We would only need to scan the mirror at the desired volume per second rate (e.g., 10 Hz, which is more than manageable for a MEMS scanner). In these embodiments, either the 2D or linear SCAPE designs could be employed. Laser light may need to be relayed down a fiber bundle. This laser light could be produced by a miniaturized laser diode/GRIN lens configuration at the proximal tip. LED light could also be used, but it should be collimated.

According to additional embodiments, endoscopic or laparoscopic data may be obtained intraluminally (e.g., in a colon, esophagus, aorta, other blood vessels, etc.) by using a rotating coupler that spirals to cover a large area. These embodiments are referred to as circumferential scanning. Although SCAPE receives a full dimension (i.e., the depth dimension) instantly, using circumferential scanning may increase the ability to cover large volumes/areas and can improve both speed and coverage.

In any of the foregoing embodiments, instead of a laser, collimated incoherent light from a non-laser source may be used, for example, a LED. Here, the problem of speckling may be avoided reducing the need for further filters for removing speckling. In any of the foregoing embodiments, the light source (laser or other) may be selected for excitation of natural fluorophores or fluorophores introduced for contrast enhancement. Examples of fluorescent contrast agents include Fluorescein, Sulforhodamine 101, proflavin and Methylene blue. In the various embodiments, the light for imaging may be one or a combination of fluorescent light from sources excited by the excitation light from the identified light source or reflected or scattered light.

In any embodiment, where a beam splitter is used to separate returning fluorescent light from excitation light, reflected as well as fluorescent light can both be applied to the detector through the use of, for example, a dichroic beam splitter and/or acousto-optic tunable filter etc. In such embodiments, the beam splitter may have a predetermined magnitude of wavelength selectivity such that some selected percentage of reflected light from the excitation beam is conveyed to the detector.

In any embodiments where a beam relay is employed, the optical elements that make up the excitation and imaging arms may be incorporated within the beam relay to reduce the number of elements required to relay the image to the end. For example, in the embodiment of FIG. 1E, elements 151-155, 125, 126, 131, 132 and 140 can be incorporated in the beam relay. In this example, the scanner may be provided in an elbow as described with reference to FIG. 2D or the beam path may be straightened using an additional reflective element 145 as in FIG. 1F. If a beam splitter is used, it may also be incorporated in the beam relay. Of course, in such embodiments, the term beam relay does not fully describe the function of such a device since it is also conditioning outgoing and incoming light as described with regard to SCAPE embodiments. It should be clear that other portions of the beam paths could be incorporated in the beam relay component as well and the above is merely an example.

Optionally, real-time analysis and display of the images captured by the systems described above can be used to provide real-time sequences of sections, orthogonal sections, 3D rendering and/or combination thereof. Optionally, the images may be rendered in color or monochromatically. Optionally, the images may be viewed remotely during acquisition (e.g., using robotic acquisition). Optionally, the images captured using any of the approaches described above may be stitched together to form large 3D volumes for subsequent zoom/interrogation in different dimensions. Optionally, embodiments that include stitching involve finding forward and/or backward planes even though the imaging head might be moving backward and forward. The depth information inherent in SCAPE systems is particularly useful because without this depth information, it can be very difficult to track between adjacent images, in which case it will be difficult to register those images for stitching. Optionally, automated recognition of patterns and feedback on tissue type may be provided, optionally combined with stitching or tissue sampling, marking or ablation/treatment. Optionally, captured images may be archived for later viewing, remote viewing, or storing to provide a medical record of histology.

Advantageously, the embodiments described above acquires either a complete plane of pixels having a depth direction (for those embodiments with a 2D sensor) or a line of pixels having a depth direction (for those embodiments with a 1D sensor) at any given instant. This provides a dramatic speed advantage with respect to competing technologies where only a single depth can be imaged at any given instant. This speed advantage is particularly useful for in vivo imaging, because the subject being imaged will either be moving (e.g., in the case of the heart) or at the very least, susceptible to movement.

It will be appreciated that the modules, processes, systems, and sections described above can be implemented in hardware, hardware programmed by software, software instruction stored on a non-transitory computer readable medium or a combination of the above. For example, a method for controlling the scanning and de-scanning elements and for sampling and storing image data and for constructing three-dimensional models from the image data can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, Lab VIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems, optics, digital data filtering, optical sensor systems and/or computer programming arts.

Moreover, embodiments of the disclosed method, system, and computer program product can be implemented in software executed on a programmed general-purpose computer, a special purpose computer, a microprocessor, or the like.

It is, thus, apparent that there is provided, in accordance with the present disclosure, SCAPE-based imaging system. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. An imaging apparatus comprising:
a catheter;
a first lens disposed at a distal portion of the catheter;
a scanning element that scans a sheet of excitation light towards the first lens, wherein the scanning element is disposed at the distal portion of the catheter, and wherein the scanning element is positioned with respect to the first lens so that the first optical component that the sheet of excitation light encounters after leaving the scanning element is the first lens, wherein the first lens is arranged to route the excitation light into tissue located outside the catheter, and to route detection light arriving from the tissue back towards the scanning element, and wherein the scanning element reflects the detection light that arrives via the first lens in a first direction;
a second lens disposed at the distal portion of the catheter in front of the scanning element in the first direction, wherein the second lens is positioned to accept the detection light that was reflected by the scanning element, and wherein the second lens routes the detection light received from the scanning element onto a tilted intermediate image plane; and
a camera optically positioned to capture images at the tilted intermediate image plane.

2. The apparatus of claim 1, further comprising:
a laser having an output;
an optical fiber positioned to route light from the output of the laser through the catheter and towards the scanning element; and
an optical element disposed at the distal end of the optical fiber, wherein the optical element is configured to create the sheet of excitation light from light arriving via the optical fiber.

3. The apparatus of claim 2, wherein the optical element comprises a GRIN lens.

4. The apparatus of claim 2, wherein the optical element comprises a scanning element.

5. The apparatus of claim 1, further comprising:
a light source disposed in the distal portion of the catheter, the light source having an output; and
an optical element disposed in the distal portion of the catheter, wherein the optical element creates the sheet of excitation light from light arriving from the output of the light source.

6. The apparatus of claim 5, wherein the optical element comprises a GRIN lens.

7. The apparatus of claim 5, wherein the optical element comprises a scanning element.

8. The apparatus of claim 1, wherein the camera comprises an image sensor positioned at the tilted intermediate image plane.

9. The apparatus of claim 1, wherein the camera comprises:
- an image sensor positioned at a position that is remote from the tilted intermediate image plane; and
- a fiber optic bundle that routes light from the tilted intermediate image plane to the 2D image sensor, wherein the fiber optic bundle has a distal face that is angled and positioned so as to coincide with the tilted intermediate image plane.

10. The apparatus of claim 9, wherein the fiber optic bundle comprises an n by m bundle of fibers, and wherein $m \geq 2n$.

11. The apparatus of claim 1, wherein the camera comprises a linear image sensor positioned at the tilted intermediate image plane.

12. The apparatus of claim 1, wherein the camera comprises:
- a linear image sensor positioned at a position that is remote from the tilted intermediate image plane; and
- a fiber optic bundle that routes light from the tilted intermediate image plane to the linear image sensor, wherein the fiber optic bundle has a distal face that is angled and positioned so as to coincide with the tilted intermediate image plane.

13. The apparatus of claim 12, wherein the fiber optic bundle comprises an n by m bundle of fibers, and wherein $m \geq 2n$.

14. The apparatus of claim 1, wherein the first lens has an outer face that faces distally beyond the catheter.

15. The apparatus of claim 1, wherein the first lens has an outer face that is sideways-facing with respect to the catheter.

* * * * *

UNITED STATES PATENT AND TRADEMARK OFFICE
CERTIFICATE OF CORRECTION

PATENT NO. : 11,317,787 B2
APPLICATION NO. : 17/074751
DATED : May 3, 2022
INVENTOR(S) : Elizabeth Marjorie Clare Hillman It is certified that error appears in the above-identified patent and that said Letters Patent is hereby corrected as shown below:

In the Specification

Column 1, Line 20, please replace "NS063228" with -- NS063226 --

Signed and Sealed this
Twentieth Day of February, 2024

Katherine Kelly Vidal
Director of the United States Patent and Trademark Office